United States Patent [19]

Obata et al.

[11] Patent Number: 5,073,558
[45] Date of Patent: Dec. 17, 1991

[54] AMINOPYRIMIDINE DERIVATIVE AND INSECTICIDE OR BACTERICIDE CONTAINING THE DERIVATIVE

[75] Inventors: Tokio Obata; Katsutoshi Fujii; Isamu Narita; Shoji Shikita, all of Ube, Japan

[73] Assignee: Ube Industries, Ltd., Ube, Japan

[21] Appl. No.: 427,818

[22] Filed: Oct. 26, 1989

Related U.S. Application Data

[63] Continuation-in-part of Ser. No. 394,197, Aug. 15, 1989, abandoned.

[30] Foreign Application Priority Data

Aug. 19, 1988 [JP] Japan .................. 63-204728
Nov. 30, 1988 [JP] Japan .................. 63-300996

[51] Int. Cl.⁵ .................. C07D 239/42; C07D 401/12; C07D 413/12; A01N 43/54
[52] U.S. Cl. .................. 514/259; 514/256; 514/258; 514/253; 514/233.5; 514/252; 514/233.8; 514/234.5; 514/234.2; 514/235.8; 544/295; 544/327; 544/328; 544/329; 544/278; 544/253; 544/283; 544/284; 544/116; 544/117; 544/121; 544/122

[58] Field of Search .................. 514/259, 256, 233.5, 514/234.5; 544/329, 295, 278, 283, 121

[56] References Cited

U.S. PATENT DOCUMENTS 3,845,055 10/1974 Hoegerle et al. .................. 544/329
3,876,636 4/1975 Fauran et al. .................. 544/329

*Primary Examiner*—John M. Ford
*Attorney, Agent, or Firm*—Frishauf, Holtz, Goodman & Woodward

[57] ABSTRACT

Disclosed are an aminopyrimidine compound or an acid addition salt thereof represented by the formula:

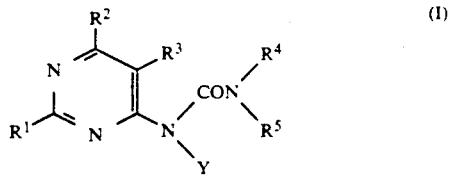

(I)

wherein R1, R2, R3, R4, R5 and Y have the same meanings defined in the specification;

a process for preparing the compound and insecticide or bactericide containing the compound.

32 Claims, No Drawings

AMINOPYRIMIDINE DERIVATIVE AND INSECTICIDE OR BACTERICIDE CONTAINING THE DERIVATIVE

This application is a continuation-in-part application of application Ser. No. 07/394,197 filed Aug. 15, 1989, now abandoned.

BACKGROUND OF THE INVENTION

This invention relates to an aminopyrimidine derivative, a method for preparing the same and a bactericide or insecticide containing the same as the active ingredient.

Heretofore, a large number of aminopyrimidine derivatives have been known. For example, Journal of American Chemical Society (J.A.C.S) 80, 2189 (1958) discloses 4-benzylamino-6-chloropyrimidine and 4-furylamino-6-chloropyrimidine as the intermediate for a diuretic, but these compounds were not recognized to have activity as agricultural chemicals.

Also, Japanese Unexamined Patent Publication Nos. 17123/1979, 76803/1980 and 76804/1980 disclose quinazoline derivatives, Japanese Unexamined Patent Publications Nos. 36666/1984, 36667/1984, 42387/1984, 286373/1986 and 67/1987 disclose various pyrimidine derivatives. These compounds all have insecticidal, acaricidal and bactericidal activities, and are known to be effective against various injurious insects, mites and diseases in agriculture and horticulture such as diamondback moth, aphid, citrus red mite, two-spotted spider mite, etc., and also blast, tomato blight, tomato downy mildew, cucumber downy mildew, etc.

However, the above known compounds, cannot be expected to have penetration migratability when sprayed onto plants, and hence are limited in application scenes. Further, they were not satisfactory in aspects of toxicity to warm blooded animals and fish toxicity.

The present inventors have studied intensively in order to solve the problems of pyrimidine derivatives of the prior art, and consequently fount that a novel compound having a carbamoyl group introduced into the amino group at the 4-position of the aminopyrimidine represented by the formula shown below exhibits excellent insecticidal, acaricidal, nematocidal, bactericidal effects, particularly having the specific feature of penetrating and migrating downward to control nematodes at the root portion even when applied to stalks and leaves. Further, it was also found that toxicity to warm blooded animals and fish toxicity have been remarkably improved.

SUMMARY OF THE INVENTION

The present invention provides an aminopyrimidine derivative represented by the formula:

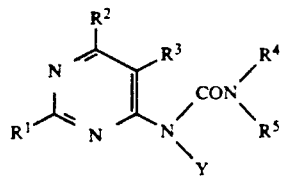

wherein $R^1$ represents hydrogen atom, a $C_{1-4}$ alkyl group, a $C_{3-6}$ cycloalkyl group or a halogen atom;

$R^2$ and $R^3$ which may be the same or different, each represent a $C_{1-4}$ alkyl group or a halogen atom, or $R^2$ and $R^3$ together with the carbon atom to which they are bonded may be a saturated or unsaturated 5-membered or 6-membered ring which may be interrupted with O or S atom fused to the pyrimidine ring, and said ring may be substituted with 1 or 2 lower alkyl group or halogen atom;

$R^4$ and $R^5$ which may be the same or different, each represent hydrogen atom, a $C_{1-4}$ alkyl group, a formyl group, an aralkyl group or a substituted or nonsubstituted phenyl group, or $R^4$ and $R^5$ together with the nitrogen atom to which they are bonded may be a saturated or unsaturated 5-membered or 6-membered ring which may be interrupted with N, O or S atom, and said ring may be fused with a carbon ring, and further said ring may be substituted with 1 or 2 $C_{1-4}$ alkyl group, halogen atom, substituted or nonsubstituted phenyl group or phenylimino group;

Y represents a group of the formula:

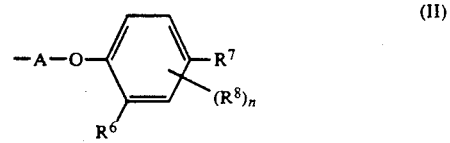

or the formula:

wherein,

A represents a $C_{2-6}$ straight or branched alkylene group;

$R^6$ and $R^8$ which may be the same or different, each represent hydrogen atom, a $C_{1-4}$ alkyl group or a halogen atom;

n represents an integer of 1 or 2;

$R^7$ represents hydrogen atom, a $C_{2-5}$ alkenyl group, a dioxolanylmethyl group which may be substituted with 1 or 2 $C_{1-4}$ alkyl group, an ethoxyimino alkyl group or a $C_{1-10}$ alkyl group which may be substituted with $C_{1-4}$ alkoxy, $C_{3-5}$ alkenyloxy, $C_{3-5}$ alkynyloxy or benzyloxy;

$R^9$ represents hydrogen tom or a $C_{1-4}$ alkyl group;

m represents an integer of 4 to 15;

$R^{10}$ represents a $C_{1-4}$ alkyl group, a $C_{1-4}$ alkoxy group, a halogen atom, an acetoxy group or a substituted or nonsubstituted phenoxy group.

or an acid addition salt thereof;

a process for preparing the same; and an insecticide or bactericide containing the same as the active ingredient.

In the above formula (I), as the $C_{1-4}$ alkyl, there may be included methyl, ethyl, propyl, isopropyl, butyl, isobutyl, sec-butyl and t-butyl.

The $C_{3-6}$ cycloalkyl may include cyclopropyl, cyclobutyl, cyclopentyl and cyclohexyl.

The halogen atom may include fluorine, chlorine, bromine and iodine.

The aralkyl group may include benzyl, α-methylbenzyl, α-ethylbenzyl, phenylethyl and the like.

The $C_{2-5}$ alkenyl group may include vinyl, allyl, 1-propenyl, methallyl and others.

The C$_{1-4}$ alkoxy group may include methoxy, ethoxy, propoxy, isopropoxy, butoxy, isobutoxy, sec-butoxy and t-butoxy.

The C$_{3-5}$ alkenyl oxy group may include allyloxy, 1-propenyloxy, methallyloxy and others.

The C$_{3-5}$ alkynyloxy group may include propargyloxy, 1-propynyloxy group and the like.

The C$_{2-6}$ straight or branched alkylene group may include ethylene, propylene, butylene, pentylene, 1-methylethylene, 2-methylethylene, 1-ethylethylene, 2-ethylethylene, 1-methylpropylene, 2-methylpropylene, 1-methylbutylene and the like.

As the substitutent of the substituted phenyl group or the substituted phenoxy group, there may be included 1 to 3 halogen atoms, C$_{1-4}$ alkyl groups, C$_{2-5}$ alkenyl groups, C$_{1-4}$ alkoxy groups, C$_{3-5}$ alkenyloxy groups, C$_{3-5}$ alkynyloxy groups, trifluoromethyl group, nitro group and others.

Examples of the 5-membered or 6-membered ring of R$^2$ and R$^3$ together with the carbon to which they are bonded which may be interrupted with O or S atom fused to the pyrimidine ring may include:

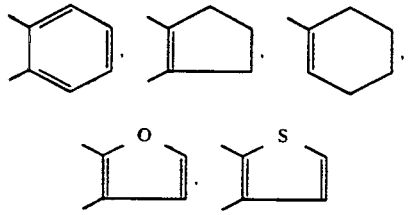

Examples of the ring which is a saturated or unsaturated 5-membered or 6-membered ring of R$^4$ and R$^6$ together with the nitrogen atom to which they are bonded which may be interrupted with O, N or S atom may include:

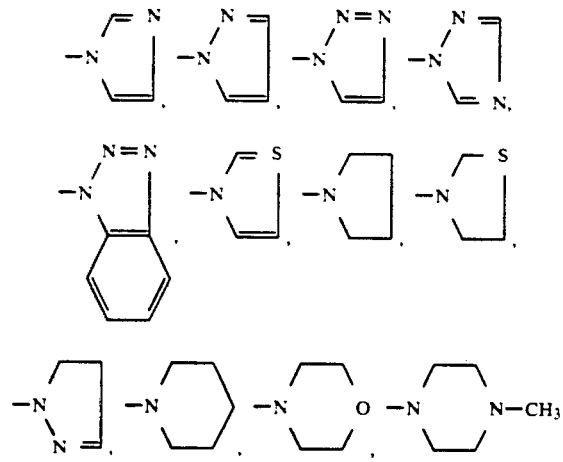

In the above formula (I), when any one of carbon atoms is asymmetric, individual optical isomers, racemic compounds or mixtures of them are also included in the present invention.

As can be understood from the above formula (I), the compounds of the present invention have amino group and can readily form acid addition salts, and such salts are also included in the present invention. The acid for forming acid addition salt may include, for example, inorganic acids such as hydrochloric acid, hydrobromic acid, nitric acid, sulfuric acid, phosphoric acid; carboxylic acids such as formic acid, oxalic acid, fumaric acid, adipic acid, stearic acid, oleic acid, aconitic acid; organic sulfonic acids such as methanesulfonic acid, benzensulfonic acid, p-toluene-sulfonic acid.

Of the compounds represented by the above formula (I), preferable ones are as follows.

R$^1$ should be preferably hydrogen atom.

When R$^2$ and R$^3$ are C$_{1-4}$ alkyl groups, methyl, ethyl and propyl are preferred, and when they are halogen atoms, chlorine and bromine atoms are preferred.

It is particularly preferred that R$^2$ should be methyl or ethyl, and R$^3$ methyl, ethyl, chlorine or bromine atom.

When R$^2$ and R$^3$ together with the carbon atom to which they are bonded form a saturated or unsaturated 5-membered or 6-membered ring which may be interrupted with O or S atom fused to the pyrimidine ring, the rings of:

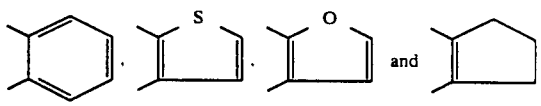

are preferred, particularly

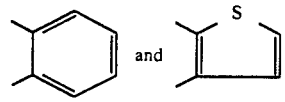

R$^4$ and R$^5$ should be preferably a saturated or unsaturated 5-membered or 6-membered ring together with the nitrogen atom to which they are bonded which may be interrupted with O, N or S atom, for example, imidazol-1-yl, pyrazol-1-yl, 1,2,3-triazol-1-yl, 1,2,4-triazol-1-yl, 2-methylimidazol-1-yl, 4-methylimidazol-1-yl and 2-phenylimino-1,3-thiazolin-1-yl. Particularly, imidazol-1-yl and pyrazol-1-yl are preferred.

The compound wherein Y has a formula of the formula (II) or (III) is preferred.

R$^6$ should be preferably methyl, ethyl and isopropyl, particularly methyl.

R$^7$ may be preferably dioxolanylmethyl group which may be substituted with 1 or 2 C$_{1-4}$ alkyl group such as 1,3-dioxolane-2-yl-methyl, 4-methyl-1,3-dioxolane-2-yl-methyl and 2,2-dimethyl-1,3-dioxolane-4-yl-methyl, and C$_{1-10}$ alkyl group such as methyl, ethyl, propyl, butyl, hexyl, octyl, nonyl, an ethyl group substituted with C$_{1-4}$ alkoxy, C$_{2-5}$ alkenyloxy, C$_{3-5}$ alkynyloxy or benzyl such as 2-methoxyethyl, 2-ethoxyethyl, 2-propoxyethyl, 2-butoxyethyl, 2-allyoxyethyl, 2-proparglyoxyethyl and 2-benzyloxyethyl.

R$^8$ should be preferably hydrogen atom or methyl group.

In the substituents of R$^6$, R$^7$ and R$^8$, further preferable combinations are R$^6$ which is methyl, R$^7$ which is 2-methoxyethyl, 2-ethoxyethyl or 2-benzyloxyethyl, and R$^8$ is hydrogen atom.

A should preferably be an ethylene group.

R$^9$ should preferably be hydrogen atom.

R$^{10}$ should preferably methyl group, methoxy group or ethoxy group.

m should be preferably 5 to 10, particularly 7 and 8.

More preferably, the compound (I) of the present invention is represented by the formulae:

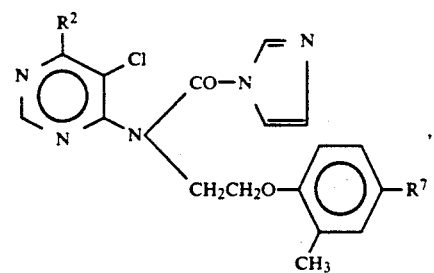

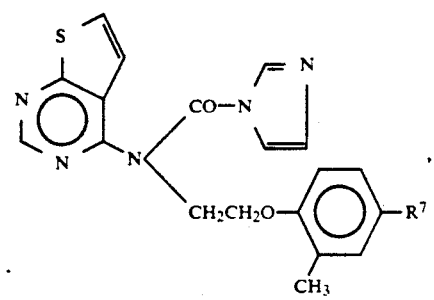

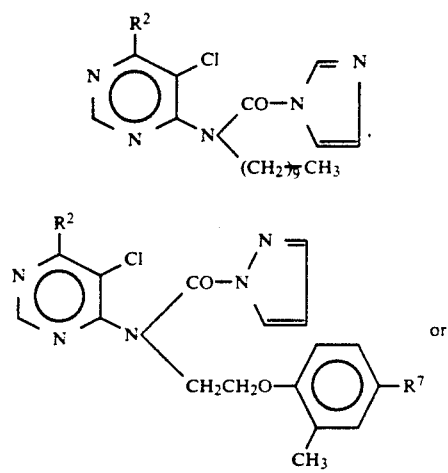

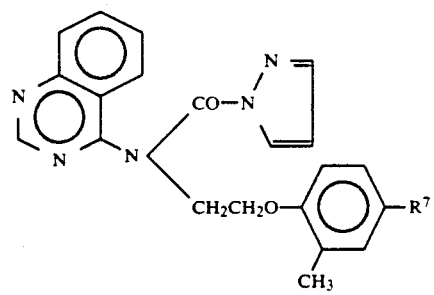

, wherein $R^2$ is —CH$_3$ or —C$_2$H$_5$ and $R^7$ is —CH$_2$CH$_2$OC$_2$H$_5$, —CH$_2$CH$_2$OCH$_2$CH=CH$_2$, —(CH$_2$)$_4$—OCH$_3$ or —CH$_2$CH$_2$OC$_3$H$_7$—n.

As specific aminopyrimidine derivatives according to the present invention, there may be mentioned those prepared in the following Examples as shown in Table 1 below.

Among derivatives as shown in Table 1, those having Compound Nos. II-1, II-19, II-24, II-33, II-34, II-35, II-57, II-73, II-82 and III-2 are particularly preferable.

The compounds (I) of the present invention are prepared according to the method shown below.

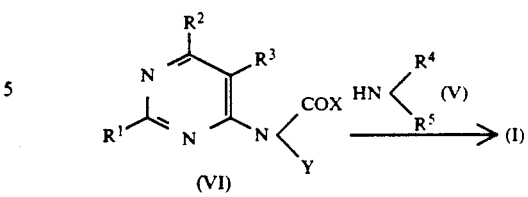

wherein $R^1$, $R^2$, $R^3$, $R^4$, $R^5$ and Y have the same meanings as defined above, and X represents a halogen atom.

As is apparent from the above reaction scheme, since an acid is eliminated in the present reaction, for permitting the reaction to proceed smoothly by trapping the acid, it is preferable to carry out the reaction in the presence of a base.

The reaction is generally carried out in the presence of a solvent. The solvent is not particularly limited, so long as it does not participate in the present reaction, including aromatic, aliphatic, alicyclic hydrocarbons which are chlorinated or not, such as benzene, toluene, xylene, methylnaphthalene, petroleum ether, ligroin, hexane, chlorobenzene, dichlorobenzene, methylene chloride, chloroform, dichloroethane, trichloroethylene, cyclohexane; ethers such as diethyl ether, ethylene glycol dimethyl ether, tetrahydrofuran, dioxane; ketones such as acetone, methyl ethyl ketone; amides such as N,N-dimethylformamide, N,N-dimethylacetamide; and mixtures of the above solvents.

As the base, there may be included organic bases such as triethylamine, pyridine, N,N-dimethylaniline, etc.; alkali metal alkoxides such as sodium methoxide, sodium ethoxide; inorganic bases such as sodium hydride, sodium amide, sodium hydroxide, potassium hydroxide, sodium carbonate, potassium carbonate, etc., preferably organic bases such as triethylamine, pyridine, etc.

Further, for accelerating the reaction rate, it is preferable to add a catalytic amount of 4-N,N-dialkylaminopyridines such as 4-N,N-dimethylaminopyridine, 4-N,N-pyrrolidinopyridine, etc.

The reaction temperature is not particularly limited, and may be generally 0° C. or higher to the boiling point of the solvent used or less, but preferably the reaction may be carried out at 5° C. to room temperature.

In the above preparation method, the compound of the formula (II) used as the starting material can be readily prepared according the method know per se.

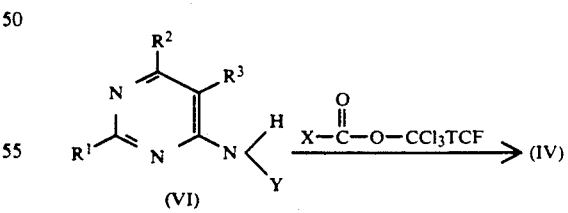

wherein $R^1$, $R^2$, $R^3$, X and Y have the same meanings as defined above, and TCF is abbreviation of trichloromethylhalogen formate.

Since hydrochloric acid is eliminated in the present reaction, for permitting the reaction to proceed smoothly by trapping this, it is preferable to carry out the reaction in the presence of a base.

The reaction is generally carried out in the presence of a solvent. The solvent is not particularly limited, so long as it does not participate in the present reaction, and the solvents to be used for the reaction between the formula (IV) and the formula (V) can be used.

As the base, there may be included organic bases such as triethylamine, pyridine, N,N-dimethylaniline, etc., preferably organic bases such as triethylamine, pyridine, etc.

The reaction temperature is not particularly limited, and may be generally 0° C. or higher to the boiling point of the solvent used or less, but preferably the reaction may be carried out at 5° C. or less.

The compound of the formula (IV) obtained in the present reaction can be also used without isolation and purification for the subsequent reaction with the compound of the formula (V).

In the present preparation method, of the compounds of the formula (VI) used as the starting material, those wherein Y has the formula (II) can be readily prepared according to the methods as described in the patent literatures as mentioned above, for example, Japanese Unexamined Patent Publications Nos. 17123/1979, 76803/1980, 76804/1980, 36666/1984, 36667/1984, 42387/1984, 286373/1986, and 67/1987.

Also, of the formula (VI), the compounds wherein Y has the formula (III) can be readily prepared according to the following method.

1. Of the compounds of the formula (VI), when $R^9$ is hydrogen atom in the formula (III) of Y:

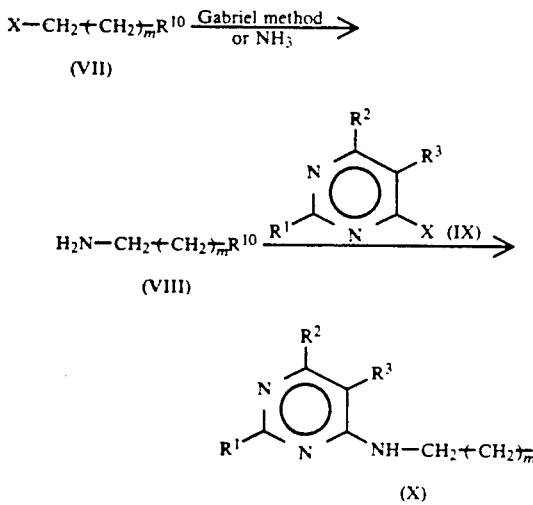

wherein $R^1$, $R^2$, $R^3$, $R^{10}$, m and X have the same meanings as defined above.

2. Of the compounds of the formula (VI), when $R^9$ is a $C_{1-4}$ alkyl in the formula (III) of Y:

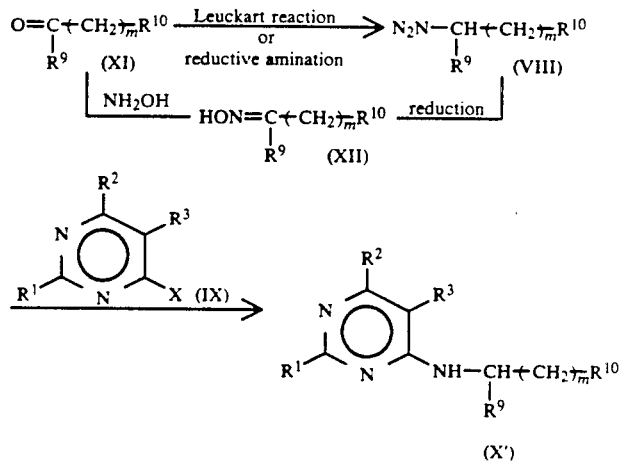

wherein $R^1$, $R^2$, $R^3$, $R^9$, $R^{10}$, and X have the same meanings as defined above.

The desired product (I) obtained by the above method can be suitably purified according to known means such as recrystallization, various chromatographies, etc.

The acid addition salt can be readily obtained by dissolving the compound of the formula (I) in an appropriate solvent, for example, aromatic, aliphatic, alicyclic hydrocarbons which are chlorinated or not, such as benzene, toluene, xylene, methylnaphthalene, petroleum ether, ligroin, hexane, chlorobenzene, dichlorobenzene, methylene chloride, chloroform, dichloroethane, trichloroethylene, cyclohexane; ethers such as diethyl ether, ethylene glycol dimethyl ether, tetrahydrofuran, dioxane; ketones such as acetone, methyl ethyl ketone, and introducing an acid during the reaction, or by introducing an acid into the reaction mixture after completion of the reaction.

The compounds (I) of the present invention exhibit excellent effects against agricultural and horticultural injurious insects, including Hemiptera such as planthoppers, leafhoppers, aphids, whiteflies, etc,; Lipidoptera such as cabbage armyworms, diamondback moth, leaf folding worms, pyralid moths, common cabbage worms, etc.; Coleoptera such as weevils, leaf beatles, etc.; and otherwise Acarina such as citrus red mite, two-spotted spider mite, etc. Also, they are extremely effective for control of hygienically injurious insects such as flies, mosquitos, cockroaches, etc. and otherwise also effective against injurious insects to stored grains, etc.

Further, the compounds (I) of the present invention are also extremely effective against root-knot nematodes, pine wood nematode, bulb mites in soil. Particularly, against root-knot nematodes, they exhibit excellent effect either by soil treatment or by stalk and leaf treatment. Accordingly, in the present invention, insecticide is used in broad sense, including insecticide in narrow sense, acaricide, nematocide and others.

Also, the compounds of the present invention are effective against agricultural and horticultural diseases such as blast, barley powdered mildew, and otherwise cucumber downy mildew, tomato disease, etc.

Thus, the compounds of the present invention have extremely wide uses and application fields, having high activities and can be provided for practical applications in various preparation forms.

The insecticide and bactericide of the present invention comprises one or several kinds of the compounds of the formula (I) as the active ingredient. Although the compound of the formula (I) itself may be used, but it is generally used by formulating conventional carriers, surfactants, dispersing agents or auxiliary agents, etc. in conventional manner to be prepared into such compositions as powder, wettable powder, emulsion, fine granule, granule, aqueous or oily suspension, aerosol, etc. before use.

Suitable carriers may include, for example, solid carriers such as talc, bentonite, clay, kaolin, diatomaceous earth, white carbon, vermiculite, slaked lime, silica sand, ammonium sulfate, urea, etc.; hydrocarbons such as kerosine, mineral oil, etc.; liquid carriers, for example, aromatic hydrocarbons such as benzene, toluene, xylene, etc.; chlorinated hydrocarbons such as chloroform, carbon tetrachloride, etc.; ethers such as dioxane, tetrahydrofuran, etc.; ketones such as acetone, cyclohexanone, isophorone, etc.; esters such as ethyl acetate, ethylene glycol acetate, dibutyl maleate, etc.; alcohols such as methanol, n-hexanol, ethylene glycol, etc.; polar solvents such as dimethylformamide, dimethyl sulfoxide, etc.; or water. Also, as the gaseous carrier, by use of air, nitrogen, carbon dioxide, Freon, etc., mixed jetting can be effected.

Also, as the surfactant, dispersing agent for effecting improvement of attachment, absorption of the present agent onto animals and plants, as well as improvement of performances of the medicament such as dispersion, emulsification, spreading, etc., there may be employed, for example, alcohol sulfates, alkylsulfonic acid salts, ligninsulfonic acid salts, polyoxyethylene glycol ethers, etc.

Further, for ameliorating the properties of the preparation, as the auxiliary agent, for example, carboxymethyl cellulose, polyethylene glycol, gum arabic, etc.

The above carrier, surfactant, dispersing agent and auxiliary agent may be used either individually or in combination depending on the respective purposes.

The concentration of the active ingredient when the compound (I) of the present invention is formed into a preparation may be generally 1 to 50% by weight for emulsion, generally 0.3 to 25% by weight for powder, generally 1 to 90% by weight for wettable powder, generally 0.5 to 5% by weight for granule, generally 0.5 to 5% by weight for oil, generally 0.1 to 5% by weight for aerosol.

These preparations can be provided for various uses depending on the respective purposes by diluting them into appropriate concentrations, and spraying on the stalks and leaves of plants, soil, water surface of paddy field, or by direct application.

The present invention is described below in more detail by referring to Examples, by which the present invention is not limited at all.

Reference example 1

Synthesis of
5-chloro-N-chlorocarbonyl-N-{2-[4-(2-ethoxyethyl)-2-methylphenoxy]ethyl}-6-methyl-4-pyrimidine amine An amount 2.0 g of trichloromethyl chloroformate (TCF) was dissolved in 30 ml of toluene and cooled to 5° C. or lower. To the solution was added dropwise a solution of 5.0 g of 5-chloro-N-{2-[4-(2-ethoxyethyl)2-methylphenoxy]ethyl}-6-methyl-4-pyrimidine amine and 1.8 g of triethylamine dissolved in 20 ml of toluene, and after the dropwise addition, the mixture was stirred at room temperature for 3 hours. After completion of the reaction, 20 ml of water was added, and the mixture was stirred at room temperature for one hour to decompose excessive TCF.

The toluene layer was separated, washed with water, dried over anhydrous sodium sulfate, followed by evaporation of the solvent under reduced pressure, to give 6.0 g of the title compound as pale yellow oily liquid.

EXAMPLE 1

Synthesis of
5-chloro-N-{2-[4-(2-ethoxyethyl)-2-methylphenoxy]ethyl}-N-(imidazol-1-yl-carbonyl)-6-methyl-4-pyrimidine amine (Compound No. II-1)

Into 10 ml of toluene was dissolved 0.4 g of imidazole and 0.6 g of triethylamine, and into the resultant solution was added under stirring a solution of 2.0 g of 5-chloro-N-chlorocarbonyl-N-{2-[4-(2-ethoxyethyl)-2-methylphenoxy]ethyl}-6-methyl-4-pyrimidine amine dissolved in 10 ml of toluene, and the mixture was stirred at room temperature for one hour. After completion of the reaction, the triethylamine hydrochloride formed was separated by filtration and washed with a small amount of toluene. The filtrate and the washing were combined, the solvent was evaporated under reduced pressure, and the resulting pale yellow oily product was isolated by column chromatography (Wako Gel C-200, eluted with toluene:ethyl acetate=3:1) to give 2.0 g of the title product as colorless crystals. m.p. 87°–88° C.

EXAMPLE 2

Synthesis of
5-chloro-N-{2-[4-(2-ethoxyethyl)-2-methylphenoxy]ethyl}-6-methyl-N-(N'-methylcarbamoyl)-4-pyrimidine amine (Compound No. II-5)

Into a solution of 1.0 g of 5-chloro-N-chlorocarbonyl-N-{2-[4-(2-ethoxyethyl)-2-methylphenoxy]ethyl}-6-methyl-4-pyrimidine amine dissolved in 20 ml of toluene was added under stirring 1 ml of an aqueous 40% monomethylamine solution, and the mixture was stirred at room temperature for one hour.

After completion of the reaction, the toluene layer was separated, washed with water, dried over anhydrous sodium sulfate, and the solvent was evaporated under reduced pressure. The crystals obtained were recrystallized from toluene-n-hexane to give 1.0 g of the title product as colorless powdery crystals. m.p. 109°–111° C.

EXAMPLE 3

Syntheses of
5-chloro-N-{2-[4-(2-ethoxyethyl)-2-methylphenoxy]ethyl}-6-methyl-N-(N'-methyl-N'-phenylcarbamoyl)-4-pyrimidine amine (Compound No. II-7)

Into a solution of 1.0 g of 5-chloro-N-chlorocarbonyl-N-{2-[4-(2-ethoxyethyl)-2-methylphenoxy]ethyl}-6-methyl-4-pyrimidine amine dissolved in 20 ml of toluene were added under stirring a mixed solution of 0.29 g of N-methylaniline, 1 ml of triethylamine and a catalytic amount of 4-N,N-dimethylaminopyridine, and the mixture was stirred at room temperature for 4 hours.

After completion of the reaction, the triethylamine hydrochloride formed was separated by filtration and washed with a small amount of toluene. The filtrate and the washing were combined, and the solvent was evaporated under reduced pressure The pale yellow oily product obtained was isolated by column chromatography (Wako Gel C-200, eluted with toluene:ethyl acetate=3:1) to give 0.85 g of the title product as colorless oily liquid. $n_D^{26.2}$ 1.5682.

EXAMPLE 4

Synthesis of
N-{2-[4-(2-ethoxyethyl)-2-methylphenoxy]-ethyl}-6-ethyl-N-(1,2,4-triazol-1-yl-carbonyl)-4-thieno[2,3-d]pyrimidine amine (Compound No. II-27)

Into a solution of 0.4 g of imidazole and 0.6 g of triethylamine dissolved in 20 ml of toluene was added dropwise under stirring a solution of 2.25 g of N-chlorocarbonyl-N-{2-[4-(2-ethoxyethyl)-2-methylphenoxy]ethyl}-4-thieno[2,3-d]pyrimidine amine dissolved in 10 ml of toluene, and the mixture was stirred at room temperature for 3 hours.

After completion of the reaction, the triethylamine hydrochloride formed was separated by filtration and washed with a small amount of toluene. The filtrate and the washing were combined, the solvent was evaporated under reduced pressure, and the pale yellow oily product obtained was isolated by column chromatography (Wako Gel C-200, eluted with toluene:ethyl acetate=2:1), and further recrystallized from toluene-n-hexane to give 1.5 g of the title product as colorless powdery crystals. m.p. 129°–131° C.

EXAMPLE 5

Synthesis of
N-{2-[4-(2-methoxyethyl)-2-methylphenoxy]-ethyl}-N-(imidazol-1-yl-carbonyl)-4-quinazoline amine (Compound No. II-38)

An amount 1.0 g of trichloromethyl formate was dissolved in 20 ml of toluene and cooled to 5° C. or lower. Into the solution were added dropwise under stirring a solution of 1.68 g of N-{2-[4-(2-methoxyethyl)-2-methylphenoxy]ethyl}4-quinazoline amine and 0.9 g of triethylamine dissolved in 10 ml of toluene, and after the dropwise addition, the mixture was stirred at room temperature for 2 hours. Subsequently, 0.4 g of imidazole and 0.6 g of triethylamine were added, followed by stirring at room temperature for one hour. After completion of the reaction, the triethylamine hydrochloride formed was separated by filtration, and washed with a small amount of toluene. The filtrate and the washing were combined, the solvent was evaporated under reduced pressure and the pale yellow oily product obtained was isolated by column chromatography (Wako Gel C-200, eluted with toluene:ethyl acetate=1:1) to give 2.0 g of the title product as colorless oily liquid. $n_D^{28.6}$ 1.5933.

EXAMPLE 6

Synthesis of
N-[2-(2-methyl-4-n-propylphenoxy)ethyl]-N-(pyrazol-1-yl-carbonyl)-4-quinazoline amine (Compound No. II-44)

In to a solution of 0.5 g of pyrazole and 0.8 g of triethylamine dissolved in 20 ml of toluene was added dropwise under stirring a solution of 2.7 g of N-chlorocarbonyl-N-[2-(2-methyl-4-n-propylphenoxy)-ethyl]-4-quinazoline amine dissolved in 10 ml of toluene, and after the dropwise addition, the mixture was stirred at room temperature for 3 hours.

After completion of the reaction, the triethylamine hydrochloride formed was separated by filtration and washed with a small amount of toluene. The filtrate and the washing were combined, the solvent was evaporated under reduced pressure and the crystals obtained were recrystallized from toluene-n-hexane to give 2.0 g of the title product as colorless needle crystals. m.p. 114°–115° C.

Reference example 2

Synthesis of
5-chloro-N-chlorocarbonyl-N-n-decyl-6-ethyl-4-pyrimidine amine

An amount 3.3 g of trichloromethylchloro formate (TCF) was dissolved in 30 ml of toluene, cooled to 5° C. or lower, and to the resultant solution was added dropwise under stirring a solution of 5.0 g of 5-chloro-N-n-decyl-6-ethyl-4-pyrimidine amine and 6.8 g of triethylamine dissolved in 30 ml of toluene. After the dropwise addition, the mixture was stirred at room temperature for 5 hours. After completion of the reaction, 20 ml of water was added and the mixture was stirred at room temperature for 30 minutes to decompose excessive TCF.

The toluene layer was separated, washed with water and dried over anhydrous sodium sulfate, followed by evaporation of the solvent under reduced pressure, to give 5.5 g of the title product as pale yellow oily liquid.

EXAMPLE 7

Synthesis of
5-chloro-N-n-decyl-N-(imidazol-1-yl-carbonyl)-6-ethyl-4-pyrimidine amine (Compound No. III-2)

Into a solution of 0.4 g of imidazole and 0.7 g of triethylamine dissolved in 10 ml of toluene was added under stirring a solution of 1.5 g of 5-chloro-N-chlorocarbonyl-N-n-decyl-6-ethyl-4-pyrimidine amine dissolved in 10 ml of toluene, and the mixture was stirred at room temperature for one hour. After completion of the reaction, the triethylamine hydrochloride formed was separated by filtration and washed with a small amount of toluene. The filtrate and the washing were combined, the solvent was evaporated under reduced pressure and a pale yellow oily product obtained was isolated by column chromatography (Wako Gel C-200, eluted with toluene:ethyl acetate=3:1) to give 1.5 g of the title product as colorless oily liquid. $n_D^{27.8}$ 1.5190.

EXAMPLE 8

Synthesis of
5-chloro-N-n-decyl-6-ethyl-N-(pyrazol-1-yl-carbonyl)-4-pyrimidine amine (Compound III-3)

Into a solution of 0.4 g of pyrazole and 0.7 g of triethylamine dissolved in 10 ml of toluene was added under stirring a solution of 1.5 g of 5-chloro-N-chlorocarbonyl-N-n-decyl-6-ethyl-4-pyrimidine amine dissolved in 10 ml of toluene, and further a catalytic amount of 4-dimethylaminopyridine (DMAP) was added, followed by stirring at room temperature for 3 hours. After completion of the reaction, the triethylamine hydrochloride formed was separated by filtration and washed with a small amount of toluene. The filtrate and the washing were combined, and a pale yellow oily product obtained by evaporation of the solvent under reduced pressure was isolated by column chromatography (Wako Gel C-200, eluted with toluene:ethyl acetate=9:1) to give 1.6 g of the title product as colorless oily liquid. $n_D^{28.0}$ 1 5182.

EXAMPLE 9

Synthesis of N-n-decyl-N-(imidazol-1-yl-carbonyl)-4-quinazoline amine (Compound III-23)

Into a solution of 0.5 g of imidazole and 0.7 g of triethylamine dissolved in 20 ml of toluene was added dropwise under stirring a solution of 1.8 g of N-chlorocarbonyl-N-n-decyl-4-quinazoline amine dissolved in 10 ml of toluene, and the mixture was stirred at room temperature for one hour. After completion of the reaction, the triethylamine hydrochloride formed was separated by filtration and washed with a small amount of toluene. The filtrate and the washing were combined, and a pale yellow product obtained by evaporation of the solvent under reduced pressure was isolated by column chromatography (Wako Gel C-200, eluted with toluene:ethyl acetate=3:1) to give 1.6 g of the title product as pale yellow oily liquid. $n_D^{23.2}$ 1 5536.

EXAMPLE 10

Synthesis of N-n-decyl-N-(2-methylimidazol-1-yl-carbonyl)-4-thieno[2,3-d]pyrimidine amine (Compound No. III-27)

Into a solution of 0.5 g of 2-methylimidazole and 0.7 g of triethylamine dissolved in 20 ml of toluene was added dropwise under stirring a solution of 1.8 g of N-chlorocarbonyl-N-n-decyl-4-thieno[2,3-d]pyrimidine amine dissolved in 10 ml of toluene, and further a catalytic amount of 4-dimethylaminopyridine (DMAP) was added, followed by stirring at room temperature for 3 hours. After completion of the reaction, the triethylamine hydrochloride formed was separated by filtration and washed with a small amount of toluene. The filtrate and the washing were combined, and the pale yellow oily product obtained by evaporation of the solvent under reduced pressure was isolated by column chromatography (Wako Gel C-200, eluted with toluene:ethyl acetate=3:1) to give 1.5 g of the title compound as pale yellow oily liquid. $n_D^{24.2}$ 1.5563.

EXAMPLE 11

In addition to the compounds prepared in Examples 1 to 10, other aminopyrimidine derivatives according to the present invention as shown in Table 1 were prepared in the similar manner as in the above Examples.

TABLE 1

[Structure: pyridine ring with R1, R2, R3 substituents; N-CON(R4)(R5) group connected via A to phenyl ring bearing R6, R7, and (R8)n]

| Compound No. | R2,R3 / R1 pyridine | R4R5N- | R6 | R7 | (R8)n | A | Physical property |
|---|---|---|---|---|---|---|---|
| II-1 | 4-Cl, 3-CH3, R1=CH3 | imidazol-1-yl | CH3 | -CH2CH2OC2H5 | H | -(CH2)2- | m.p. 87~88° |
| II-2 | " | pyrazol-1-yl | " | " | " | " | m.p. 67~68° |
| II-3 | " | imidazol-1-yl | " | " | " | " | m.p. 98~100° |
| II-4 | " | 1,2,4-triazol-1-yl | " | " | " | " | $n_D^{26.2}$ 1.5608 |
| II-5 | " | -NHCH3 | " | " | " | " | m.p. 109~111° |
| II-6 | " | -N(CH3)2 | " | " | " | " | $n_D^{26.4}$ 1.5421 |

TABLE 1-continued

| | | | | | |
|---|---|---|---|---|---|
| II-7 | ⟨structure: N-methyl-N-phenyl with 3-Cl-pyridine⟩ | ⟨structure: N-methylanilino⟩ | " | " | $n_D^{26.2}$ 1.5682 |
| II-8 | " | ⟨piperidino⟩ | " | " | m.p. 63~65° |
| II-9 | " | ⟨morpholino⟩ | " | " | m.p. 83~84° |
| II-10 | " | ⟨2,6-dimethylmorpholino⟩ | $CH_3$ | $-CH_2CH_2OC_2H_6$ | H | $+CH_2\rightarrow$ | $n_D^{26.8}$ 1.5461 |
| II-11 | " | ⟨N-methylpiperazino⟩ | " | " | m.p. 91~92° |
| II-12 | " | ⟨2-methylimidazolyl⟩ | " | " | $n_D^{26.6}$ 1.5549 |
| II-13 | " | ⟨4-methylimidazolyl⟩ | " | " | $n_D^{26.2}$ 1.5595 |

TABLE 1-continued

| No. | Ar | Het | R1 | R2 | R3 | Property |
|---|---|---|---|---|---|---|
| II-14 | (4-Cl, 3-C₂H₅, pyridine) | (benzotriazole) | " | " | " | $n_D^{27.8}$ 1.5758 |
| II-15 | " | (pyrazole) | i-C₃H₆ | H | " | m.p. 104~106° |
| II-16 | " | " | CH₃ | —CH₂CH=CH₂ | " | $n_D^{26.0}$ 1.5671 |
| II-17 | " | " | " | —CH₂-(1,3-dioxolane) | " | $n_D^{26.0}$ 1.5607 |
| II-18 | " | " | " | —CH₂CH₂OC₂H₆ | 3-CH₃ | m.p. 98~100° |
| II-19 | (4-Cl, 3-C₂H₅, pyridine) | " | " | " | H | $n_D^{24.0}$ 1.5585 |
| II-20 | " | " | " | CH₃ | 3-CH₃ | $n_D^{23.4}$ 1.5622 |
| II-21 | " | (pyrazole) | CH₃ | CH₃ | H | $n_D^{26.3}$ 1.5581 ⧽CH₂⧽ |
| II-22 | " | " | " | —CH₂CH₂OCH₃ (Ph) | " | $n_D^{26.0}$ 1.5787 |
| II-23 | " | " | i-C₃H₇ | H | " | $n_D^{25.6}$ 1.5626 |

TABLE 1-continued

| | | | | |
|---|---|---|---|---|
| II-24 | 3,5-dichloro-2-methylpyridine ($C_3H_{7-n}$, Cl) | " | $CH_3$ | $-CH_2CH_2OC_2H_5$ | " | " | $n_D^{26.0}$ 1.5514 |
| II-25 | 3-chloro-4-methyl-pyridine ($CH_3$, Cl) | " | " | " | " | m.p. 79~81° |
| II-26 | thieno-pyridine | " | " | " | " | $n_D^{26.4}$ 1.5868 |
| II-27 | | imidazolyl-N | " | " | " | m.p. 129~131° |
| II-28 | methyl-thieno-pyridine ($CH_3$) | imidazolyl-N | " | " | " | $n_D^{26.0}$ 1.5841 |
| II-29 | quinoline | " | i-$C_3H_7$ | H | " | m.p. 126~128° |

TABLE 1-continued

| | | | | | | |
|---|---|---|---|---|---|---|
| II-30 | ![pyridine with Cl, CH3, CH3] | " | CH3 | " | " | m.p. 85–87° |
| II-31 | ![pyridine with Cl, CH3, CH3] | imidazolyl | CH3 | -CH2-CH(CH3)-O-CH2-O (methyldioxolane) | " | $n_D^{26.4}$ 1.5610 |
| II-32 | ![pyridine with Cl, CH3, CH3] | " | CH3 | -CH2-C(CH3)2-O-CH2-O | H | $-(CH_2)_7-$ $n_D^{26.1}$ 1.5516 |
| II-33 | ![pyridine with Cl, CH3, CH3] | " | " | $-CH_2CH_2OC_3H_{7-n}$ | " | $n_D^{26.4}$ 1.5559 |
| II-34 | ![pyridine with Br, CH3, CH3] | " | " | $-CH_2CH_2OC_2H_6$ | " | $n_D^{26.4}$ 1.5639 |
| II-35 | ![cyclopentapyridine] | " | " | " | " | $n_D^{26.2}$ 5664 |

TABLE 1-continued

| No. | Structure 1 | Structure 2 | R | Sub | nD |
|---|---|---|---|---|---|
| II-36 | C₃H₇-n, Cl, pyrimidine | [S,N-phenyl thiazoline] | " | 3-CH₃ | $n_D^{26.4}$ 1.5575 |
| II-37 | C₂H₅, Cl, pyrimidine | imidazole (N-) | CH₃ | H | $n_D^{27.0}$ 1.5960 |
| II-38 | quinoline | " | —CH₂CH₂OCH₃ | " | $n_D^{28.6}$ 1.5933 |
| II-39 | CH₃-furo[pyrimidine] | " | —CH₂CH₂OC₂H₅ | 5-CH₃ | $n_D^{28.6}$ 1.5793 |
| II-40 | " | " | " | 3,5-(CH₃)₂ | $n_D^{28.6}$ 1.5721 |
| II-41 | " | " | —CH₂CH₂OCH₂-C₆H₅ | H | $n_D^{28.6}$ 1.5798 |
| II-42 | thieno[pyrimidine] | " | —CH₂CH₂OCH₃ | " | $n_D^{28.6}$ 1.6017 |

TABLE 1-continued
| | | CH₃ | -n-C₃H₇ | H | ⁺CH₂⁷⁄₇ | |
|---|---|---|---|---|---|---|
| II-43 | 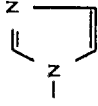 | " | " | " | " | $n_D^{27.2}$ 1.5786 |
| II-44 | " | " | " | " | " | m.p. 114–115° |
| II-45 | 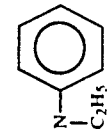 | " | " | " | " | $n_D^{27.2}$ 1.5848 |
| II-46 |  | " | " | " | " | m.p. 119–121° |
| II-47 | 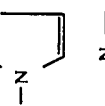 | " | " | " | " | m.p. 159–161° |
| II-48 |  | " | H | " | " | $n_D^{26.8}$ 1.5974 |
| II-49 | 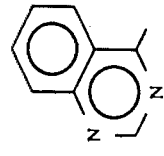 | " | " | " | " | $n_D^{26.8}$ 1.5924 |
| II-50 | 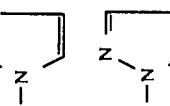 | " | " | " | " | $n_D^{26.8}$ 1.6029 |

TABLE 1-continued
| No. | | | | | | | Property |
|---|---|---|---|---|---|---|---|
| II-51 | 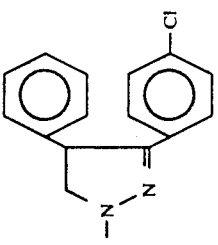 | 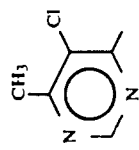 | " | " | " | " | m.p. 178~180° |
| II-52 | " | 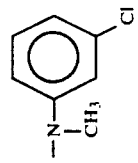 | " | —CH₂CH₂OC₂H₆ | " | " | $n_D^{27.8}$ 1.5602 |
| II-53 | " | 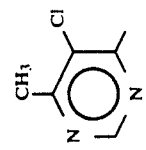 | " | " | " | " | $n_D^{27.8}$ 1.5650 |
| II-54 | 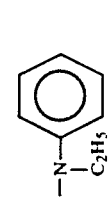 | 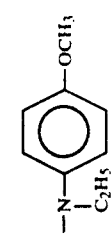 | CH₃ | —CH₂CH₂OC₂H₅ | H | ⁺CH₂)₂ | $n_D^{27.8}$ 1.5604 |
| II-55 | " | 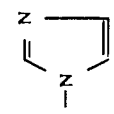 | " | " | " | " | $n_D^{27.8}$ 1.5556 |
| II-56 | " | | " | " | " | " | $n_D^{26.9}$ 1.5633 |
| II-57 | " | | " | —CH₂CH₂OCH₂CH=CH₂ | " | " | $n_D^{26.2}$ 1.5666 |

TABLE 1-continued

| | | | | | |
|---|---|---|---|---|---|
| II-58 | [pyrazole-N-Me] | " | " | " | $n_D^{26.0}$ 1.5670 |
| II-59 | [imidazole-N-Me] | " | —CH$_2$CH$_2$OCH$_2$C≡CH | " | $n_D^{25.8}$ 1.5704 |
| II-60 | [pyrazole-N-Me] | " | " | " | $n_D^{26.0}$ 1.3661 |
| II-61 | [thiazoline-N-Me] | " | " | " | $n_D^{26.7}$ 1.5790 |
| II-62 | [imidazole-N-Me] | " | H | " | $n_D^{26.2}$ 1.5998 |
| II-63 | [pyrazole-N-Me] | " | " | " | m.p. 66–68° |
| II-64 | [thiazoline-N-Ph] | " | " | " | $n_D^{26.2}$ 1.6154 |

TABLE 1-continued

| | | | CH₃ | —CH₂CH₂OC₂H₅ | H | ${+}CH_2{\rightarrow}_2$ |
|---|---|---|---|---|---|---|
| II-65 | [pyridine: Cl, CH₃, Cl, N, CH₃] | [imidazole N-N] | | | | |
| II-66 | " | [pyrazole] | " | " | " | " |
| II-67 | " | [triazole N-N-N] | " | " | " | " |
| II-68 | [pyridine: C₂H₅, Cl, CH₃, N, C₂H₅] | [imidazole] | " | " | " | " |
| II-69 | " | [pyrazole] | " | " | " | " |
| II-70 | [pyridine: C₂H₅, Cl, CH₃, N, cyclopropyl] | [triazole] | " | " | " | " |
| II-71 | " | [pyrazole] | " | " | " | " |

TABLE 1-continued

| | | | | | | |
|---|---|---|---|---|---|---|
| II-72 | (pyrimidine with C2H5, Cl, Cl substituents) | (imidazole N-Me) | " | " | " | " |
| II-73 | (quinoline with methyl) | " | " | " | " | $n_D^{27.0}$ 1.5828 |
| II-74 | " | (pyrazole N-Me) | " | H | H | $n_D^{26.4}$ 1.5874 |
| II-75 | " | (pyrazole N-Me) | H | H | " | m.p. 87~90° |
| II-76 | " | (pyrazole N-Me) | H | H | $-(CH_2)_2-$ | $n_D^{27.0}$ 1.6096 |
| II-77 | (quinoline with methyl) | (benzothiazole-N-phenyl) | " | " | " | " |

TABLE 1-continued
| No. | Ring | R1 | R2 | R3 | n |
|---|---|---|---|---|---|
| II-78 |  | CH₃ | —CH₂CH₂OC₂H₅ | | $n_D^{27.0}$ 1.5371 |
| II-79 | 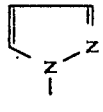 | " | " | " | $n_D^{27.4}$ 1.5507 |
| II-80 | 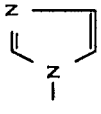 | " | " | " | |
| II-81 | " | " | —CH₂CH=NOC₂H₅ | " | |
| II-82 | " | " | ─(CH₂)₇₀CH₃ | " | $n_D^{27.0}$ 1.5818 |
| II-83 | " | " | —CH₂CH—OC₂H₅<br>         \|<br>         CH₃ | " | $n_D^{25.3}$ 1.5873 |
| II-84 | " | " | —CH₂CH—OC₂H₅<br>         \|<br>         C₂H₅ | " | $n_D^{25.4}$ 1.5892 |
| II-85 | " | " | CH₃ | 6-CH₃ | —CH₂CH—<br>     \|<br>     CH₃    $n_D^{29.2}$ 1.5768 |
| II-86 | " | " | ─(CH₂)₂CH₃ | H | ─(CH₂)₇    $n_D^{25.2}$ 1.5715 |

TABLE 1-continued

| | | | | | |
|---|---|---|---|---|---|
| II-87 | ![quinoline] | ![pyrazole N-N-CH3] | CH₃ | —CH₂CH₂CH=CHCH₃ | H | $(CH_2)_7$ | $n_D^{26.4}$ 1.5949 |
| II-88 | " | " | " | —CH₂CH₂OC₄H₉-n | " | " | $n_D^{26.4}$ 1.5723 |
| II-89 | " | ![pyrazole] | CH₃ | " | " | " | $n_D^{27.2}$ 1.5796 |
| II-90 | " | " | " | —CH₂CH₂CH=CHCH₃ | " | " | $n_D^{27.2}$ 1.6022 |
| II-91 | " | ![pyrazole N-N] | " | —C₃H₇-n | " | $(CH_2)_7$ | $n_D^{25.4}$ 1.5912 |
| II-92 | " | ![pyrazole-CH3 N-N] | " | —CH₂CH₂OC₂H₅ | " | $(CH_2)_7$ | $n_D^{23.2}$ 1.5761 |
| II-93 | ![pyridine with Cl, CH3] | —NH—C₄H₉-n | " | " | " | " | m.p. 78~80° |
| II-94 | " | —NH—C₄H₉-t | " | " | " | " | $n_D^{26.4}$ 1.5406 |
| II-95 | " | ![pyrazole N-N] | " | —C₃H₇-n | " | $(CH_2)_7$ | $n_D^{26.0}$ 1.5893 |
| II-96 | ![quinoline] | " | " | —CH₂CH₂OC₂H₅ | 6-Cl | $(CH_2)_7$ | $n_D^{25.4}$ 1.5941 |

TABLE 1-continued

| No. | Structure 1 | Structure 2 | R1 | R2 | R3 | Property |
|---|---|---|---|---|---|---|
| II-97 | C₃H₇-n, Cl, pyridyl | imidazole | " | " | " | $n_D^{25.2}$ 1.5963 |
| II-98 | quinoline | 4-methylimidazole | CH₃ | —CH₂CH₂OC₂H₅ | H | —CH₂— | $n_D^{26.0}$ 1.5513 |
| II-99 | CH₃, Cl, pyridyl | N-CHO phenyl | " | H | " | $n_D^{27.4}$ 1.5917 |
| II-100 | quinoline | N-H phenyl | " | —CH₂CH₂OC₂H₅ | " | m.p. 87~88° |
| II-101 | —NH₂ | pyrazole | i-C₃H₇ | " | " | m.p. 150~152° |
| II-102 | | pyrazole | " | H | " | $n_D^{23.1}$ 1.5842 |
| II-103 | quinoline | 2-methylimidazole | " | " | " | $n_D^{23.0}$ 1.5804 |

TABLE 1-continued

| No. | Ar | Het | R | R' | | Physical data |
|---|---|---|---|---|---|---|
| II-104 | 3-Cl-2,4-di-CH₃-pyridyl | 1-methyl-2-methyl-imidazolyl | " | " | " | m.p. 104–106° |
| II-105 | " | 2,4-di-CH₃-1-methyl-imidazolyl | " | " | " | $n_D^{23.0}$ 1.5814 |
| II-106 | 3-CH₃-2-(2,3-di-CH₃-thienyl)-pyridyl | 1-methyl-2-methyl-imidazolyl | CH₃ | —CH₂—CH—CH₂ with O—C(CH₃)₂—O | " | $n_D^{23.0}$ 1.5523 |
| II-107 | " | 1-pyrrolyl | " | —CH₂CH₂OCH₂—C₆H₅ | " | $n_D^{22.9}$ 1.6068 |
| II-108 | " | 1-pyrazolyl | " | " | " | $n_D^{23.4}$ 1.5992 |
| II-109 | 3-CH₃-2-(2,3-di-CH₃-thienyl)-pyridyl | 1-methyl-2-methyl-imidazolyl | CH₃ | —CH₂CH₂OCH₂—C₆H₅ | H ―(CH₂)₇― | $n_D^{23.1}$ 1.5971 |

TABLE 1-continued

| No. | Structure 1 | Structure 2 | R | Sub | Property |
|---|---|---|---|---|---|
| II-110 | thieno-pyridine | pyrazole (N-Me) | —CH₂CH₂OC₂H₅ | " | m.p. 85~86° |
| II-111 | " | 2-CH₃-imidazole (N-Me) | " | " | $n_D^{23.8}$ 1.5936 |
| II-112 | 4-Cl-3-CH₃-pyridine | pyrazole (N-Me) | " | 3-CH₃ | m.p. 109~111° |
| II-113 | " | pyrazole (N-Me) | —CH₂CH₂OCH₂-Ph | H | $n_D^{23.0}$ 1.5859 |
| II-114 | " | pyrazole (N-Me) | " | " | m.p. 88~89° |
| II-115 | " | 2-CH₃-imidazole (N-Me) | " | " | $n_D^{24.4}$ 1.5734 |
| II-116 | " | imidazole (N-Me) | n-C₄H₉ | " | $n_D^{23.0}$ 1.5641 |

TABLE 1-continued

| No. | | | | | |
|---|---|---|---|---|---|
| II-117 | " | pyrazole (N—N) | " | " | $n_D^{23.4}$ 1.5596 |
| II-118 | " | pyrazole | —CH$_2$—(1,3-dioxolane-C$_2$H$_5$) | " | $n_D^{21.4}$ 1.3547 |
| II-119 | " | pyrazole | " | " | $n_D^{22.6}$ 1.5647 |
| II-120 | 3-CH$_3$, 4-Cl pyridine | CH$_3$-pyrazole | —CH$_2$—(1,3-dioxolane-C$_2$H$_5$) | H | $\text{—(CH}_2\text{)—}$ $n_D^{21.4}$ 1.5524 |
| II-121 | 3-C$_2$H$_5$, 4-Cl pyridine | pyrazole | —CH$_2$C$_6$H$_5$ | " | m.p. 75–76° |
| II-122 | " | CH$_3$-pyrazole | " | " | $n_D^{21.6}$ 1.5750 |
| II-123 | " | pyrazole | —CH$_2$CH$_2$OC$_2$H$_5$ | " | $n_D^{21.4}$ 1.5580 |
| II-124 | Hydrochloride salt of Compound No. 1 | | | | *1 |
| II-125 | Hydrochloride salt of Compound No. 12 | | | | *2 |
| II-126 | Oxalic acid salt of Compound No. 1 | | | | *3 |

TABLE 1-continued

Structural formula:

$$\begin{array}{c} R^2 \\ R^3 \\ \diagdown \\ N \diagup \diagdown N \\ | \\ R^1 \end{array} \begin{array}{c} R^4 \\ CON \\ N \\ CH(CH_2)_m R^{10} \\ | \\ R^9 \end{array}$$

| Compound No. | $\begin{array}{c} R^2 \\ R^3 \\ \diagdown \\ N \diagup \diagdown N \\ | \\ R^1 \end{array}$ | $-N\begin{array}{c}R^4\\R^5\end{array}$ | $R^9$ | $R^{10}$ | m | Physical property |
|---|---|---|---|---|---|---|
| III-1 | 4-Cl, 3-C₂H₅, 6-CH₃ pyridine | N-methylimidazole | CH₃ | CH₃ | 8 | $n_D^{24.9}$ 1.5163 |
| III-2 | " | N-methylpyrazole | H | " | " | $n_D^{27.8}$ 1.5190 |
| III-3 | " | " | " | " | " | $n_D^{28.0}$ 1.5182 |
| III-4 | " | N-methylaniline | " | " | " | $n_D^{28.2}$ 1.5202 |
| III-5 | " | 2-methyl-N-methylimidazole | " | " | " | $n_D^{25.7}$ 1.5180 |

TABLE 1-continued

| | | | | |
|---|---|---|---|---|
| III-6 | [imidazole-CH₃] | " | " | $n_D^{25.7}$ 1.5189 |
| III-7 | [pyrazole] | " | " | $n_D^{25.0}$ 1.5141 |
| III-8 | [triazole] | " | " | $n_D^{25.0}$ 1.5166 |
| III-9 | [p-methoxy-N-methylanilino / chloroethylpyrimidine] | " | " | $n_D^{24.9}$ 1.5319 |
| III-10 | [imidazole] | H | CH₃ | 9 $n_D^{25.6}$ 1.5225 |
| III-11 | [2-methylimidazole] | " | " | $n_D^{26.1}$ 1.5183 |
| III-12 | [4-methylimidazole] | " | " | 7 $n_D^{26.3}$ 1.5186 |

TABLE 1-continued

| No. | Structure A | Structure B | R | n | Property |
|---|---|---|---|---|---|
| III-13 | " | pyrazole | " | " | $n_D^{26.4}$ 1.5222 |
| III-14 | " | imidazole | " | 5 | $n_D^{23.6}$ 1.5237 |
| III-15 | " | pyrazole | " | " | $n_D^{24.3}$ 1.5245 |
| III-16 | " | imidazole | " | 10 | $n_D^{24.4}$ 1.5139 |
| III-17 | " | pyrazole | " | " | $n_D^{24.4}$ 1.5130 |
| III-18 | | 2 COOH—COOH salt of Compound No. 2 | | | m.p. 77~79° |
| III-19 | | 2 HClO$_4$ salt of Compound No. 2 | | | |
| III-20 | 3-Cl-2,5-diCH$_3$-pyridyl | imidazole | H | CH$_3$ | 8 $n_D^{23.2}$ 1.5220 |
| III-21 | 3-Cl-2,5-diCH$_3$-pyridyl | 2-CH$_3$-imidazole | H | CH$_3$ | 8 $n_D^{23.2}$ 1.5208 |

TABLE 1-continued
| | | | | | |
|---|---|---|---|---|---|
| III-22 | 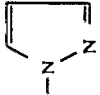 | 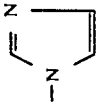 | " | " | $n_D^{23.0}$ 1.5212 |
| III-23 | " | | " | " | $n_D^{23.2}$ 1.5536 |
| III-24 | " | | " | " | $n_D^{22.6}$ 1.5476 |
| III-25 | " | | " | " | m.p. 70–71° |
| III-26 | 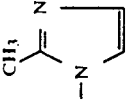 | | " | " | m.p. 56–58° |
| III-27 | " | | " | " | $n_D^{24.2}$ 1.5563 |
| III-28 | " | | " | " | m.p. 105–107° |

TABLE 1-continued

| No. | Ar1 | Het | R | Ar2 | Step | Physical constant |
|---|---|---|---|---|---|---|
| III-29 | 3-C$_2$H$_5$-4-Cl-pyridin-2-yl | imidazol-1-yl | " | 2-CH$_3$-phenoxy | 7 | $n_D^{22.8}$ 1.5503 |
| III-30 | " | 2-CH$_3$-imidazol-1-yl | " | " | " | $n_D^{22.6}$ 1.5468 |
| III-31 | 3-C$_2$H$_5$-4-Cl-pyridin-2-yl | pyrazol-1-yl | " | " | " | $n_D^{22.6}$ 1.5501 |
| III-32 | 3-C$_2$H$_5$-4-Cl-pyridin-2-yl | 2-CH$_3$-imidazol-1-yl | H | CH$_3$ | 5 | $n_D^{23.8}$ 1.5242 |
| III-33 | " | imidazol-1-yl | " | " | 10 | $n_D^{23.8}$ 1.5133 |
| III-34 | " | 2-CH$_3$-imidazol-1-yl | " | " | 6 | $n_D^{22.2}$ 1.5240 |
| III-35 | " | imidazol-1-yl | " | " | " | $n_D^{22.2}$ 1.5166 |
| III-36 | " | pyrazol-1-yl | " | " | " | $n_D^{22.2}$ 1.5248 |

TABLE 1-continued
| | | | | | |
|---|---|---|---|---|---|
| III-37 | 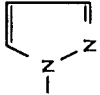 | " | " | —OCH₃ | $n_D^{23.0}$ 1.5288 |
| III-38 | 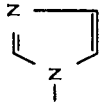 | " | " | " | $n_D^{23.0}$ 1.5260 |
| III-39 |  | " | " | —OC₂H₅ | $n_D^{22.0}$ 1.5211 |
| III-40 |  | " | " | " | $n_D^{23.0}$ 1.5101 |
| III-41 |  | " | " | Cl | $n_D^{25.6}$ 1.5342 8 |
| III-42 | 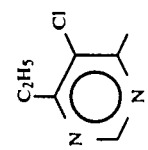 | " | " | " | $n_D^{26.6}$ 1.5326 |
| III-43 | 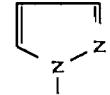 | " | H | —OCH₃ | $n_D^{25.6}$ 1.5250 7 |
| III-44 | | | " | " | $n_D^{25.6}$ 1.5247 |

TABLE 1-continued

| | | | | |
|---|---|---|---|---|
| III-45 | ![pyrazole] | " | —OCOCH$_3$ | $n_D^{24.0}$ 1.5245 |
| III-46 | ![pyrazole] | " | " | $n_D^{24.0}$ 1.5226 |
| III-47 | ![pyrazole] | " | —OC$_4$H$_9$-n | $n_D^{20.4}$ 1.5246 |
| III-48 | ![pyrazole] | " | " | $n_D^{20.2}$ 1.5230 |

In Table 1, " means the same compound as previous one in upper line.
*1Elemental analysis as C$_{22}$H$_{26}$ClN$_5$O$_3$.2HCl

| | C (%) | H (%) | N (%) |
|---|---|---|---|
| calculated: | 51.12 | 5.46 | 13.55 |
| found: | 50.87 | 5.72 | 13.36 |

*2Elemental analysis as C$_{23}$H$_{28}$ClN$_5$O$_3$.HCl.H$_2$O

| | C (%) | H (%) | N (%) |
|---|---|---|---|
| calculated: | 53.91 | 5.90 | 13.67 |
| found: | 54.10 | 6.18 | 13.40 |

*3Elemental analysis as C$_{22}$H$_{26}$ClN$_5$O$_3$.(COOH)$_2$

| | C (%) | H (%) | N (%) |
|---|---|---|---|
| calculated: | 53.99 | 5.29 | 13.12 |
| found: | 53.62 | 5.45 | 12.95 |

EXAMPLE 12

Five (5) parts by weight of the compound of Compound No. II-1, 35 parts by weight of bentonite, 57 parts by weight of talc, 1 part by weight of Neopelex powder (trade name: manufactured by Kao-Atlas) and 2 parts by weight of sodium ligninsulfonate were uniformly mixed, and subsequently kneaded with addition of a small amount of water, followed by granulation and drying, to obtain granules.

EXAMPLE 13

Ten (10) parts by weight of the compound of Compound No. II-21, 70 parts by weight of kaolin, 18 parts by weight of white carbon, 1.5 parts by weight of Neopelex powder (trade name: manufactured by Kao-Atlas) and 0.5 part by weight of Demol (trade name: manufactured by Kao-Atlas) were uniformly mixed, followed by pulverization to obtain wettable powder.

EXAMPLE 14

To 20 parts by weight of the compound of Compound No. III-1 and 70 parts by weight of xylene were added 10 parts by weight of Toxanone (trade name: manufactured by Sanyo Kasei Kogyo), and the mixture was uniformly mixed and dissolved to obtain an emulsion.

EXAMPLE 15

Five (5) parts by weight of the compound of Compound No. III-1, 50 parts by weight of talc and 45 parts of kaolins were uniformly mixed to obtain powder.

EXAMPLE 16

Activity test against diamondback moth-1

The compounds shown in Table 1 were formulated similarly as described in Example 13, and each formulation was diluted with water containing a surfactant (0.01%) to 300 ppm to prepare a chemical solution. In each chemical solution, cabbage leaf strip (5 cm ×5 cm) was dipped for 30 seconds, and placed in a plastic cup. After drying, ten 3rd instar diamondback moth larvae were freed, and the plastic cup was closed with a lid and left to stand in a thermostatic chamber of 25° C. 2 days later, the numbers of live and dead insects were counted to determine the % mortality. The results are shown in Table 2.

In Table 2, those with mortality of 100% are shown as A, those with 99 to 80% as B, those with 79 to 60% as C and those with less than 60% as D.

TABLE 2

| Compound No | Activity against diamondback moth |
|---|---|
| II - 1 | B |
| 12 | A |
| 13 | B |
| 19 | A |
| 20 | B |
| 21 | A |
| 23 | A |
| 26 | A |
| 29 | A |
| 31 | B |
| 32 | A |
| 33 | B |
| 35 | B |
| 36 | A |
| 38 | A |
| 39 | B |
| 40 | B |
| 41 | B |

TABLE 2-continued

| Compound No. | Activity against diamondback moth |
|---|---|
| 42 | B |
| 43 | B |
| 48 | B |
| 56 | B |
| 57 | B |
| 58 | B |
| 59 | B |
| 73 | A |
| 82 | A |
| 83 | B |
| 92 | B |
| 96 | A |
| 98 | A |
| 106 | B |
| 111 | B |
| 123 | A |
| 124 | A |
| 125 | A |
| 126 | A |

EXAMPLE 17

Activity test against diamondback moth-2

The compounds shown in Table 1 were formulated similarly as described in Example 13, and each formulation was diluted with water containing a surfactant (0.01%) to 1000 ppm to prepare a chemical solution. In each chemical solution, cabbage leaf strip (5 cm ×5 cm) was dipped for 30 seconds, and placed in a plastic cup. After drying, ten 3rd instar diamondback moth larvae were freed, and the plastic cup was closed with a lid and left to stand in a thermostatic chamber of 25° C. 2 days later, the numbers of live and dead insects were counted to determine the % mortality. The results are shown in Table 3.

The Table 3, those with mortality of 100% are shown as A, those with 99 to 80% as B, those with 79 to 60% as C and those with less than 60% as D.

TABLE 3

| Compound No. | Activity against diamondback moth |
|---|---|
| III - 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 18 | A |
| 19 | A |
| 23 | A |
| 24 | A |
| 25 | A |
| 26 | A |
| 27 | A |
| 28 | A |
| 30 | A |
| 31 | A |
| 32 | A |
| 33 | A |
| 34 | A |
| 36 | A |
| 37 | A |
| 39 | A |

EXAMPLE 18

Activity test against brown rice planthopper-1

The compounds shown in Table 1 were formulated similarly as described in Example 13, and each formulation was diluted with water containing a surfactant (0.01%) to 300 ppm to prepare a chemical solution. In each chemical solution were dipped young rice seedlings for 30 seconds, and the rice seedlings after air drying were inserted into a glass cylinder. Ten 3rd instar brown rice planthopper larvae were freed into the cylinder, and the cylinder was left to stand stoppered with a porous plug in a thermostatic chamber of 25° C. 4 days layer, the numbers of live and dead insects were counted to determine the % mortality. The results are shown in Table 4.

In Table 4, those with mortality of 100% are shown as A, those with 99 to 80% as B, those with 79 to 60% as C and those with less than 60% as D.

TABLE 4

| Compound No. | Activity against brown rice planthopper |
|---|---|
| II - 1 | A |
| 4 | B |
| 12 | A |
| 13 | A |
| 19 | A |
| 21 | A |
| 25 | A |
| 26 | B |
| 28 | A |
| 29 | B |
| 30 | B |
| 31 | B |
| 32 | B |
| 33 | B |
| 34 | A |
| 35 | B |
| 38 | A |
| 43 | A |
| 48 | B |
| 49 | A |
| 56 | B |
| 58 | B |
| 59 | B |
| 73 | A |
| 78 | B |
| 83 | B |
| 84 | A |
| 90 | B |
| 97 | B |
| 98 | A |
| 106 | B |
| 111 | A |
| 123 | A |
| 124 | A |
| 125 | A |
| 126 | A |

EXAMPLE 19

Activity test against brown rice planthopper-2

The compound shown in Table 1 were formulated similarly as described in Example 13, and each formulation was diluted with water containing a surfactant (0.01%) to 1000 ppm to prepare a chemical solution. In each chemical solution were dipped young rice seedlings for 30 seconds, and the rice seedlings after air drying were inserted into a glass cylinder. Ten 3rd instar brown rice planthopper larvae were freed into the cylinder, and the cylinder was left to stand stoppered with a porous plug in a thermostatic chamber of 25° C. 4 days layer, the numbers of live and dead insects were counted to determine the % mortality. The results are shown in Table 5.

In Table 5, those with mortality of 100% are shown as A, those with 99 to 80% as B, those with 79 to 60% as C and those with less than 60% as D.

TABLE 5

| Compound No. | Activity against brown rice planthopper |
|---|---|
| III - 2 | A |
| 3 | A |
| 10 | A |
| 13 | A |
| 18 | A |
| 23 | A |
| 25 | A |
| 36 | A |
| 38 | A |
| 39 | A |
| 40 | A |
| 42 | A |
| 44 | A |
| 47 | A |
| 48 | A |

EXAMPLE 20

Activity test against green rice leafhopper

The compounds shown in Table 1 were formulated similarly as described in Example 13, and each formulation was diluted with water containing a surfactant (0.01%) to 1000 ppm to prepare a chemical solution. In each chemical solution was dipped young rice seedlings for 30 seconds, and the rice seedlings after air drying were inserted into a glass cylinder. Ten 3rd instar green rice leafhopper larvae were freed into the cylinder, and the cylinder was left to stand stoppered with a porous plug in a thermostatic chamber of 25° C. 4 days later, the numbers of live and dead insects were counted to determine the % mortality.

In Tables 6-1 and Tables 6-2, those with mortality of 100% are shown as A, those with 99 to 80% as B, those with 79 to 60% as C and those with less than 60% as D.

TABLE 6-1

| Compound No. | Activity against green rice leafhopper |
|---|---|
| II - 12 | B |
| 13 | B |
| 29 | A |
| 21 | B |
| 22 | B |
| 23 | A |
| 24 | B |
| 29 | A |
| 31 | B |
| 32 | B |
| 34 | B |
| 36 | A |
| 38 | B |
| 48 | B |
| 49 | B |
| 56 | B |
| 58 | A |
| 59 | A |
| 60 | A |
| 73 | B |
| 83 | A |
| 84 | A |
| 90 | A |
| 98 | A |
| 102 | A |
| 106 | A |
| 111 | B |
| 123 | A |

TABLE 6-1-continued

| Compound No. | Activity against green rice leafhopper |
|---|---|
| 124 | A |
| 125 | B |
| 126 | A |

TABLE 6-2

| Compound No. | Activity against green rice leafhopper |
|---|---|
| III - 2 | A |
| 3 | A |
| 7 | A |
| 8 | A |
| 10 | A |
| 13 | A |
| 14 | A |
| 15 | A |
| 18 | A |
| 19 | A |
| 22 | A |
| 23 | A |
| 25 | A |
| 29 | A |
| 31 | A |
| 34 | A |
| 36 | A |
| 40 | A |
| 44 | A |
| 48 | A |

EXAMPLE 21

Activity test against female adult twospotted spider mite-1

Ten female adult two-spotted spider mites were provided for the test of kidney bean leaf strip (diameter 20 mm). On the other hand, the compounds shown in Table 1 were formulated similarly as in Example 13 and each formulation was diluted with water containing a surfactant (0.01%) to 300 ppm to prepare a chemical solution. In each chemical solution was dipped the leaf strip for 10 seconds. The strips were left to stand in a thermostatic chamber of 25° C. and 3 days later, the numbers of live and dead mites were counted to determined the % acaricide mortality, of which results are shown in Table 7

In Table 7 those with acaricide mortality of 100% are shown as A, those with 99 to 80% as B, those with 79 to 60% as C and those with less than 60% as D.

TABLE 7

| Compound No. | Activity against adult two-spotted spider mite |
|---|---|
| II - 1 | A |
| 2 | A |
| 3 | A |
| 4 | A |
| 12 | A |
| 13 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |

TABLE 7-continued

| Compound No. | Activity against adult two-spotted spider mite |
|---|---|
| 29 | A |
| 31 | A |
| 32 | A |
| 33 | A |
| 34 | A |
| 35 | A |
| 36 | B |
| 38 | A |
| 42 | A |
| 43 | B |
| 53 | B |
| 56 | A |
| 57 | A |
| 58 | A |
| 60 | A |
| 62 | A |
| 73 | A |
| 74 | A |
| 78 | A |
| 82 | A |
| 83 | A |
| 84 | A |
| 87 | A |
| 88 | A |
| 89 | A |
| 90 | A |
| 91 | A |
| 92 | A |
| 94 | A |
| 95 | B |
| 96 | A |
| 98 | A |
| 106 | A |
| 109 | B |
| 110 | A |
| 111 | A |
| 112 | A |
| 113 | A |
| 114 | A |
| 116 | A |
| 118 | A |
| 119 | A |
| 120 | A |
| 121 | A |
| 122 | A |
| 123 | A |
| 124 | A |
| 125 | A |
| 126 | A |

EXAMPLE 22

Activity test against female adult two-spotted spider mite-2

Ten female adult two-spotted spider mites were provided for the test of kidney bean leaf strip (diameter 20 mm). On the other hand, the compounds shown in Table 1 were formulated similarly as in Example 13 and each formulation was diluted with water containing a surfactant (0.01%) to 1000 ppm to prepare a chemical solution. In each chemical solution was dipped the leaf strip for 10 seconds. The strips were left to stand in a thermostatic chamber of 25° C. and 3 days later, the numbers of live and dead mites were counted to determined the % acaricide mortality, of which results are shown in Table 8

In Table 8 those with acaricide mortality of 100% are shown as A, those with 99 to 80% as B, those with 79 to 60% as C and those with less than 60% as D.

TABLE 8

| Compound No. | Activity against adult two-spotted spider mite |
|---|---|
| III - 2 | A |
| 3 | A |
| 4 | A |
| 5 | A |
| 6 | A |
| 7 | A |
| 8 | A |
| 10 | A |
| 11 | A |
| 12 | A |
| 13 | A |
| 14 | A |
| 15 | A |
| 16 | A |
| 17 | A |
| 18 | A |
| 19 | A |
| 21 | A |
| 22 | A |
| 23 | A |
| 25 | A |
| 26 | A |
| 27 | A |
| 29 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 48 | A |

EXAMPLE 23

Activity test against sweet potato root-knot nematode (1)

The compounds shown in Table 1 were formulated similarly as described in Example 12, and each formulation was diluted with water to a chemical solution of 20 ppm. Of the solution, 0.5 ml was taken into a test tube, and further 0.5 ml of a solution containing 30 to 40 sweet potato root-knot nematodes was added. The mixture was left to stand in a thermostatic chamber of 25° C., and 2 days later, the numbers of live and dead nematodes were counted under microscope to determine the % mortality. The results are shown in Table 9.

In Table 9-1 and 9-2, those with mortality of 100% to 90% are shown as A, those with 89% to 80% as B, those with 79% to 60% as C and those with less than 60% as D.

TABLE 9-1

| Compound No. | Activity against sweet potato root-knot nematode |
|---|---|
| II - 1 | A |
| 2 | B |
| 3 | A |
| 4 | A |
| 12 | A |
| 13 | A |
| 16 | A |
| 17 | A |
| 19 | B |
| 22 | A |
| 24 | A |
| 25 | A |
| 26 | A |
| 27 | A |
| 28 | A |
| 31 | B |
| 32 | A |
| 33 | A |
| 34 | B |
| 35 | A |
| 38 | A |
| 39 | B |
| 41 | B |
| 43 | A |
| 56 | A |
| 57 | A |
| 59 | B |
| 73 | A |
| 78 | B |
| 82 | A |
| 84 | A |
| 87 | B |
| 88 | A |
| 92 | A |
| 96 | B |
| 97 | A |
| 98 | A |
| 110 | B |
| 111 | B |
| 116 | B |
| 122 | B |
| 124 | A |
| 125 | A |
| 126 | A |

TABLE 9-2

| No. | Activity against sweet potato root-knot nematode |
|---|---|
| III - 2 | A |
| 5 | A |
| 6 | A |
| 10 | A |
| 11 | A |
| 12 | A |
| 14 | A |
| 18 | A |
| 19 | A |
| 24 | A |
| 26 | A |
| 27 | A |
| 34 | A |
| 35 | A |
| 39 | A |
| 41 | A |
| 43 | A |

EXAMPLE 24

Effect against sweet potato root-knot nematode (2)

The compounds shown in Table 1 were formulated similarly as described in Example 12 and diluted with water containing a surfactant (0.03%) to prepare a chemical solution of 3000 ppm. Each chemical solution was sprayed in a sufficient amount onto a potting cucumber with 2 developed leaves. On the 4th day after spraying, about 500 sweet potato root-knot nematodes per pot were inoculated, and further the goal number of nematodes was examined on the 10th day after inoculation. The results are shown in Table 10.

In Tables 10-1 and 10-2, from comparison between the goal number of the treated group and that of non-treated group, those with control value of 90% or more are shown as A, those with 89 to 70% as B, those with 69 to 50% as C and those with less than 50% as D.

TABLE 10-1

| Compound No. | Activity against sweet potato root-knot nematode |
|---|---|
| II - 1 | A |
| 13 | B |
| 19 | A |
| 24 | A |
| 28 | B |
| 33 | A |
| 34 | A |
| 35 | A |
| 38 | B |
| 56 | B |
| 57 | A |
| 59 | B |
| 73 | A |
| 78 | B |
| 82 | A |
| 84 | B |
| 87 | B |
| 88 | B |
| 92 | A |
| 98 | A |
| 111 | B |
| 124 | A |
| 125 | A |
| 126 | A |

TABLE 10-2

| Compound No. | Activity against sweet potato root-knot nematode |
|---|---|
| III - 2 | A |
| 18 | A |
| 19 | A |

We claim:
1. An aminopyrimidine compound represented by the formula (I):

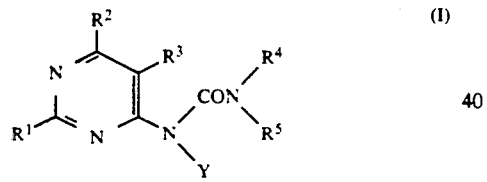

wherein
$R^1$ represents hydrogen atom, a $C_{1-4}$ alkyl group, a $C_{3-6}$ cycloalkyl group or a halogen atom;
$R^2$ and $R^3$, which may be the same or different, each represent a $C_{1-4}$ alkyl group or a halogen atom, or $R^2$ and $R^3$ together with the carbon atom to which they are bonded may be a 5-membered or 6-membered ring selected from the group consisting of

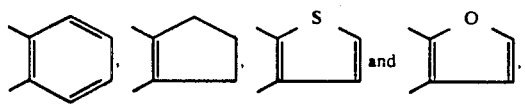

and said ring may be substituted with 1 or 2 lower alkyl groups or a halogen atom;
$R^4$ and $R^5$, which may be the same or different, each represent a hydrogen atom, a $C_{1-4}$ alkyl group, a formyl group, a phenylalkyl group, a nonsubstituted phenyl group or a phenyl group substituted by a substituent selected from the group consisting of 1 to 3 halogen atoms, $C_{1-4}$ alkyl groups, $C_{2-5}$ alkenyl groups, $C_{1-4}$ alkoxy groups, $C_{3-5}$ alkenyloxy groups, $C_{3-5}$ alkynyloxy groups, a trifluoromethyl group and a nitro group; or $R^4$ and $R^5$ together with the nitrogen atom to which they are bonded may be a 5-membered or 6-membered ring, said ring being selected from the group consisting of

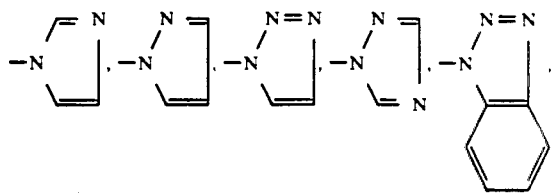

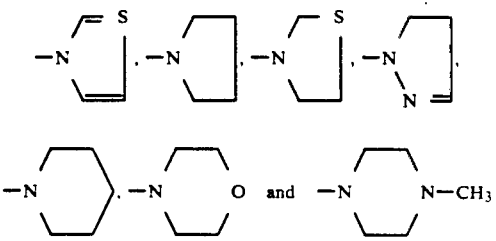

and further said ring may be substituted with 1 or 2 $C_{1-4}$ alkyl groups, a halogen atom, a nonsubstituted phenyl group, a phenyl group substituted by a substituent selected from the group consisting of 1 to 3 halogen atoms, $C_{1-4}$ alkyl groups, $C_{2-5}$ alkenyl groups, $C_{1-4}$ alkoxy groups, $C_{3-5}$ alkenyloxy groups, $C_{3-5}$ alkynyloxy groups, a trifluoromethyl group and a nitro group or a phenylimino group;
Y represents a group of the formula:

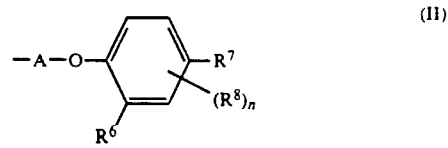

or the formula

wherein,
A represents a $C_{2-6}$ straight or branched alkylene group;
$R^6$ and $R^8$, which may be the same or different, each represent hydrogen atom, a $C_{1-4}$ alkyl group or a halogen atom;
n represents an integer of 1 or 2;
$R^7$ represents hydrogen atom, a $C_{2-5}$ alkenyl group, a dioxolanylmethyl group which may be substituted with 1 or 2 $C_{1-4}$ alkyl groups, an ethoxyimino alkyl group or a $C_{1-10}$ alkyl group which may be substituted with $C_{1-4}$ alkoxy, $C_{3-5}$ alkenyloxy, $C_{3-5}$ alkynyloxy or benzyloxy;
$R^9$ represents a hydrogen atom or a $C_{1-4}$ alkyl group;
m represents an integer of 4 to 15;
$R^{10}$ represents a $C_{1-4}$ alkyl group, a $C_{1-4}$ alkoxy group, a halogen atom, an acetoxy group or a nonsubstituted phenoxy group or a phenoxy group substituted with a substituent selected from the group consisting of 1 to 3 halogen atoms, $C_{1-4}$ alkyl groups, $C_{2-5}$ alkenyl groups, $C_{1-4}$ alkoxy groups, $C_{3-5}$ alkenyloxy groups, C$_{3-5}$ alkynyloxy groups, a trifluoromethyl group and a nitro group, or an acid addition salt thereof.

2. The compound or an acid additional salt thereof according to claim 1, wherein R$^1$ represents hydrogen atom, R$^2$ and R$^3$ each represent methyl, ethyl, propyl, chlorine or bromine, or together with the carbon atom to which they are bonded, represent a ring selected from the group consisting of

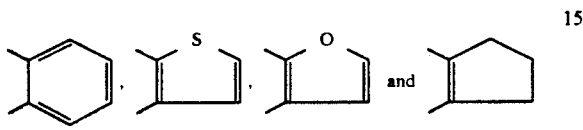

R$^4$ and R$^5$ together with the nitrogen to which they are bonded represent imidazol-1-yl, pyrazol-1-yl, 1,2,3,-triazol-1-yl, 1,2,4-triazol-1-yl, 2-methylimidazol-1-yl, 4-methylimidazol-1-yl or 2-phenylimino-1,3-thiazolin-1-yl, Y is a compound represented by the formula (II):

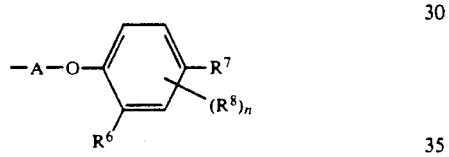

wherein

R$^6$ represents methyl, ethyl or isopropyl,

R$^7$ represents 1,3-dioxolane-2-yl-methyl, 4-methyl-1,3-dioxolane-2-yl-methyl, 2,2-dimethyl-1,3-dioxolane-4-yl-methyl, methyl, ethyl, propyl, butyl, hexyl, octyl, nonyl, 2-methoxyethyl, 2-ethoxyethyl, 2-propoxyethyl, 2-butoxyethyl, 2-allyoxyethyl, 2-propargyloxyethyl or 2-benzyloxyethyl, R$^8$ represents hydrogen atom or methyl, A represents ethylene, R$^9$ represents hydrogen atom, R$^{10}$ represents methyl, methoxy or ethoxy, m represents 5 to 10.

3. The compound according to claim 1, wherein said compound is selected from the group consisting of

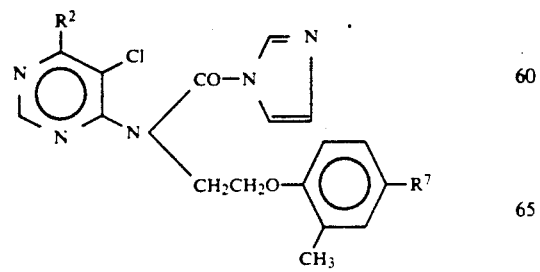

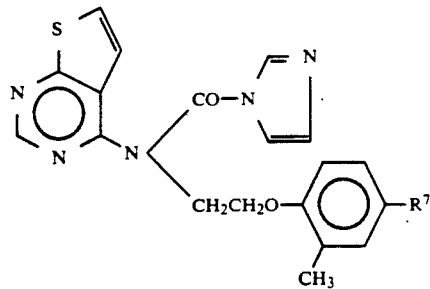

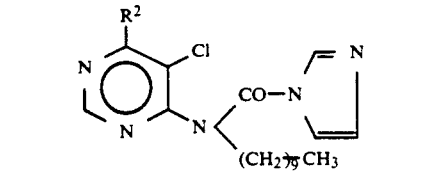

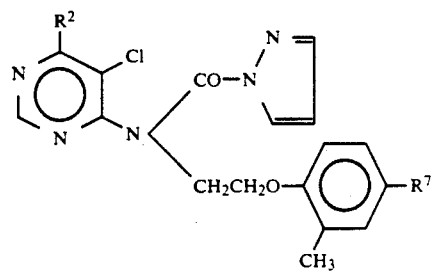

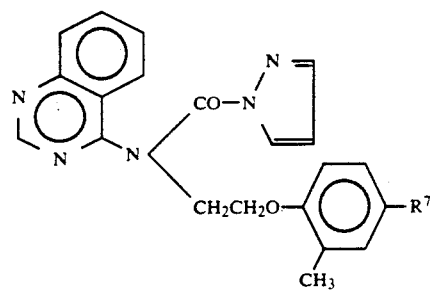

, wherein R$^2$ is —CH$_3$ or —C$_2$H$_5$ and R$^7$ is —CH$_2$CH$_2$OC$_2$H$_5$, —CH$_2$CH$_2$OCH$_2$CH=CH$_2$, —(CH$_2$)$_4$—OCH$_3$ or —CH$_2$CH$_2$OC$_3$H$_7$—n;

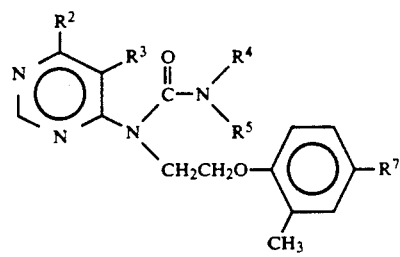

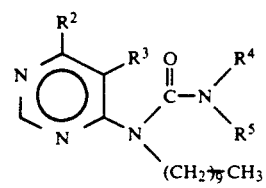

-continued

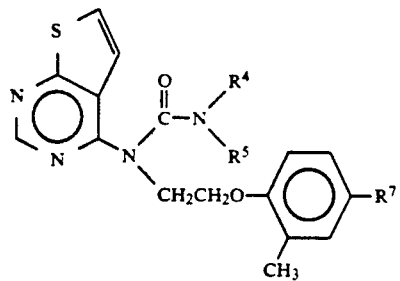

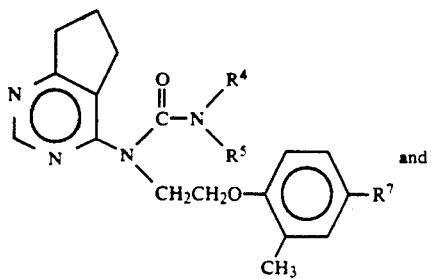

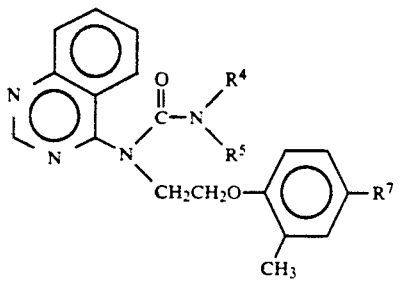

$R^2$ = —CH$_3$, —C$_2$H$_5$, —C$_3$H$_7$
$R^3$ = Cl, Br

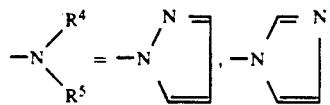

$R^7$ is —CH$_2$CH$_2$OC$_2$H$_5$, —CH$_2$CH$_2$OCH$_2$CH=CH$_2$, —(CH$_2$)$_4$—OCH$_3$ or —CH$_2$CH$_2$OC$_3$H$_7$-n.

4. The compound according to claim 3, wherein said compound is selected from the group consisting of 5-chloro-N-(2-[4-(2-ethoxyethyl)-2-methylphenoxy]ethyl)-N-(imidazol-1-ylcarbonyl)-6-n-propyl-4-pyrimidine amine, 5-chloro-N-(2-[4-(2-n-propoxyethyl)-2-methylphenoxy]ethyl)-N-(imidazol-1-ylcarbonyl)-6-methyl-4-pyrimidine amine, 5-bromo-N-(2-[4-(2-ethoxyethyl)-2-methylphenoxy]ethyl)-N-(imidazol-1-ylcarbonyl)-6-methyl-4-pyrimidine amine, N-(2-[4-(2-ethoxyethyl)-2-methylphenoxy]ethyl)-N-(imidazol-1-ylcarbonyl)-4-cyclopentapyrimidine amine, 5-chloro-N-(2-[4-(2-allyloxyethyl)-2-methylphenoxy]ethyl)-N-(imidazol-1-ylcarbonyl)-6-methyl-4-pyrimidine amine, N-(2-[4-(4-methoxybutyl)-2-methylphenoxy]ethyl)-N-(imidazol-1-ylcarbonyl)-4-quinazoline amine and 5-chloro-N-n-decyl-N-(imidazol-1-ylcarbonyl)-6-ethyl-4-pyrimidine amine.

5. An insecticide composition comprising a carrier, and as the active ingredient, an insecticidally effective amount of the compound of claim 1.

6. A bactericide composition comprising a carrier, and as the active ingredient, a bactericidally effective amount of the compound of claim 1.

7. The compound or acid addition salt thereof according to claim 1, wherein $R^4$ and $R^5$ together with the nitrogen atom to which they are bonded form a saturated or unsaturated 5-membered or 6-membered ring selected from the group consisting of imidazole, pyrazole, 1,2,4-triazole, 1,2,3-triazole, 2-methylimidazole, 3-methylimidazole, 2,3-dimethylimidazole, thiazolidine, 2-phenyliminothiazolidine, 3-(4-chlorophenyl)-4-phenyl-4,5-dihydropyrazole, benzotriazole, piperidine, morpholine, 2,6-dimethylmorpholine and 4-methylpiperazine.

8. The compound or acid addition salt thereof according to claim 1, wherein $R^4$ and $R^5$, which may be the same or different, each represent a phenyl group substituted by a substituent selected from the group consisting of 1 to 3 halogen atoms, $C_1$-$C_4$ alkyl groups and $C_1$-$C_4$ alkoxy groups.

9. The compound or acid addition salt thereof according to claim 1, wherein $R^4$ and $R^5$ together with the nitrogen atom to which they are bonded form a saturated or unsaturated 5-membered or 6-membered ring and said ring being substituted with a phenyl group substituted by a halogen.

10. The insecticide composition according to claim 5, wherein $R^4$ and $R^5$ together with the nitrogen atom to which they are bonded form a saturated or unsaturated 5-membered or 6-membered ring selected from the group consisting of imidazole, pyrazole, 1,2,4-triazole, 1,2,3-triazole, 2-methylimidazole, 3-methylimidazole, 2,3-dimethylimidazole, thiazolidine, 2-phenyliminothiazolidine, 3-(4-chlorophenyl)-4-phenyl-4,5-dihydropyrazole, benzotriazole, piperidine, morpholine, 2,6-dimethylmorpholine and 4-methylpiperazine.

11. The bactericide composition according to claim 6, wherein $R^4$ and $R^5$ together with the nitrogen atom to which they are bonded form a saturated or unsaturated 5-membered or 6-membered ring selected from the group consisting of imidazole, pyrazole, 1,2,4-triazole, 1,2,3-triazole, 2-methylimidazole, 3-methylimidazole, 2,3-dimethylimidazole, thiazolidine, 2-phenyliminothiazolidine, 3-(4-chlorophenyl)-4-phenyl-4,5-dihydropyrazole, benzotriazole, piperidine, morpholine, 2,6-dimethylmorpholine and 4-methylpiperazine.

12. A method for combating insects comprising applying to insects or to a habitat thereof an insecticidally effective amount of the compound according to claim 1 or an acid addition salt thereof, either alone or in admixture with a carrier.

13. A method for combating bacteria comprising applying to plants, soil, a water surface of a paddy field or to a habitat thereof a bacterially effective amount of the compound according to claim 1 or an acid addition salt thereof, either alone or in admixture with a carrier.

14. The aminopyrimidine compound or acid addition salt thereof according to claim 1, wherein the compound is 5-chloro-N-(2-[4-(2-ethoxyethyl)-2-methylphenoxy]ethyl)-N-(imidazol-1-ylcarbonyl)-6-methyl-4-pyrimidine amine.

15. The aminopyrimidine compound or acid addition salt thereof according to claim 1, wherein the compound is 5-chloro-N-(2-[4-(2-ethoxyethyl)-2-methylphenoxy]ethyl)-N-(imidazol-1-ylcarbonyl)-6-ethyl-4-pyrimidine amine.

16. The aminopyrimidine compound or acid addition salt thereof according to claim 1, wherein the compound is N-(2-[4-(2-ethoxyethyl)-2-methylphenoxy]ethyl)-N-(imidazol-1-ylcarbonyl)-4-quinazoline amine.

17. The insecticide composition according to claim 5, wherein the compound is 5-chloro-N-(2-[4-(2-ethoxyethyl)-2-methylphenoxy]ethyl)-N-(imidazol-1-ylcarbonyl)-6-methyl-4-pyrimidine amine or an acid addition salt thereof.

18. The insecticide composition according to claim 5, wherein the compound is 5-chloro-N-(2-[4-(2-ethoxyethyl)-2-methylphenoxy]ethyl)-N-(imidazol-1-ylcarbonyl)-6-ethyl-4-pyrimidine amine or an acid addition salt thereof.

19. The insecticide composition according to claim 5, wherein the compound is N-(2-[4-(2-ethoxyethyl)-2-methylphenoxy]ethyl)-N-(imidazol-1-ylcarbonyl)-4-quinazoline amine or an acid addition salt thereof.

20. The insecticide composition according to claim 5, wherein the compound is selected from the group consisting of
5-chloro-N-(2-[4-(2-ethoxyethyl)-2methylphenoxy]ethyl)-N-(imidazol-1-ylcarbonyl)-6-n-propyl-4-pyrimidine amine,
5-chloro-N-(2-[4-(2-n-propoxyethyl)-2-methylphenoxy]ethyl)-N-(imidazol-1-ylcarbonyl)-6-methyl-4pyrimidine amine,
5-bromo-N-(2-[4-(2-ethoxyethyl)-2-methylphenoxy]ethyl)-N-(imidazol-1-ylcarbonyl)-6-methyl-4-pyrimidine amine,
N-(2-[4-(2-ethoxyethyl)-2-methylphenoxy]ethyl)-N-(imidazol-1-ylcarbonyl)-4-cyclopentapyrimidine amine,
5-chloro-N-(2-[4-(2-allyloxyethyl)-2-methylphenoxy]ethyl)-N-(imidazol-1-ylcarbonyl)-6-methyl-4-pyrimidine amine,
N-(2-[4-(4-methoxybutyl)-2-methylphenoxy]ethyl)-N-(imidazol-1-ylcarbonyl)-4-quinazoline amine,
5-chloro-N-n-decyl-N-(imidazol-1-ylcarbonyl)-6ethyl-4-pyrimidine amine and acid addition salts thereof.

21. The bactericide composition according to claim 6, wherein the compound is 5-chloro-N-(2-[4-(2-ethoxyethyl-2-methylphenoxy]ethyl)-N-(imidazol-1-ylcarbonyl)-6-methyl-4-pyrimidine amine or an acid addition salt thereof.

22. The bactericide composition according to claim 6, wherein the compound is 5-chloro-N-(2-[4-(2-ethoxyethyl)-2-methylphenoxy]ethyl)-N-(imidazol-1-ylcarbonyl)-6-ethyl-4-pyrimidine amine or an acid addition salt thereof.

23. The bactericide composition according to claim 6, wherein the compound is N-(2-[4-(2-ethoxyethyl)-2-methylphenoxy]ethyl)-N-(imidazol-1-ylcarbonyl)-4-quinazoline amine or an acid addition salt thereof.

24. The bactericide composition according to claim 6, wherein the compound is selected from the group consisting of
5chloro-N-(2-[4-(2-ethoxyethyl)-2-methylphenoxy]ethyl)-N-(imidazol-1-ylcarbonyl)-6n-propyl-4-pyrimidine amine,
5-chloro-N-(2-[4-(2-n-propoxyethyl)-2-methylphenoxy]ethyl)-N-(imidazol-1ylcarbonyl)-6methyl-4-pyrimidine amine,
5-bromo-N-(2-[4-(2-ethoxyethyl)-2-methylphenoxy]ethyl)-N-(imidazol-1-ylcarbonyl)-6 -methyl-4-pyrimidine amine,
N-(2-[4-(2-ethoxyethyl)-2-methylphenoxy]ethyl)-N-(imidazol-1-ylcarbonyl)-4-cyclopentapyrimidine amine,
5-chloro-N-(2-[4-(2-allyloxyethyl)-2methylphenoxy]ethyl)-N-(imidazol-1-ylcarbonyl)-6-methyl-4pyrimidine amine,
N-(2-[4-(4-methoxybutyl)-2-methylphenoxy]ethyl)-N-(imidazol-1-ylcarbonyl)-4-quinazoline amine,
5-chloro-N-n-decyl-N-(imidazol-1-ylcarbonyl)-6-ethyl-4-pyrimidine amine and acid addition salts thereof.

25. The method for combating insects according to claim 12, wherein the compound is 5-chloro-N-(2-[4-(2-ethoxyethyl)-2-methylphenoxy]ethyl)-N-(imidazol-1-ylcarbonyl)-6-methyl-4-pyrimidine amine or an acid addition salt thereof.

26. The method for combating insects according to claim 12, wherein the compound is 5-chloro-N-(2-[4-(2-ethoxyethyl)-2-methylphenoxy]ethyl)-N-(imidazol-1-ylcarbonyl)-6-ethyl-4-pyrimidine amine or an acid addition salt thereof.

27. The method for combating insects according to claim 12, wherein the compound is N-(2-[4-(2-ethoxyethyl)-2-methylphenoxy]ethyl)-N-(imidazol-1-ylcarbonyl)-4-quinazoline amine or an acid addition salt thereof.

28. The method for combating insects according to claim 12, wherein the compound is selected from the group consisting of
5-chloro-N-(2-[4-(2-ethoxyethyl)-2-methylphenoxy]ethyl)-N-(imidazol-1-ylcarbonyl)-6-n-propyl-4-pyrimidine amine,
5-chloro-N-(2-[4-(2-n-propoxyethyl)-2-methylphenoxy]ethyl)-N-(imidazol-1-ylcarbonyl)-6-methyl-4-pyrimidine amine,
5-bromo-N-(2-[4-(2ethoxyethyl)-2methylphenoxy]ethyl)-N-(imidazol-1-ylcarbonyl)-6-methyl-4-pyrimidine amine,
N-(2-[4-(2-ethoxyethyl)-2-methylphenoxy]ethyl)-N-(imidazol-1-ylcarbonyl)-4-cyclopentapyrimidine amine,
5-chloro-N-(2-[4-(2-allyloxyethyl)-2-methylphenoxy]ethyl)-N-(imidazol-1-ylcarbonyl)-6-methyl-4-pyrimidine amine
N-(2-[4-(4methoxybutyl)-2-methylphenoxy]ethyl)-N-(imidazol-1-ylcarbonyl)-4-quinazoline amine,
5-chloro-N-n-decyl-N-(imidazol-1-ylcarbonyl)-6-ethyl-4-pyrimidine amine and acid addition salts thereof.

29. The method for combating bacteria according to claim 13, wherein the compound is 5-chloro-N-(2-[4-(2-ethoxyethyl)-2-methylphenoxy]ethyl)-N-(imidazol-1-ylcarbonyl)-6-methyl-4-pyrimidine amine or an acid addition salt thereof.

30. The method for combating bacteria according to claim 13, wherein the compound is 5-chloro-N-(2-[4-(2-ethoxyethyl)-2-methylphenoxy]ethyl)-N-(imidazol-1-ylcarbonyl)-6-ethyl-4-pyrimidine amine or an acid addition salt thereof.

31. The method for combating bacteria according to claim 13, wherein the compound is N-(2-[4-(2-ethoxyethyl)-2-methylphenoxy]ethyl)-N-(imidazol-1-ylcarbonyl)-4-quinazoline amine or an acid addition salt thereof.

32. The method for combating bacteria according to claim 13, wherein the compound is selected from the group consisting of
5-chloro-N-(2-[4-(2-ethoxyethyl)-2-methylphenoxy]ethyl)-N-(imidazol-1-ylcarbonyl)-6-n-propyl-4-pyrimidine amine, 5-chloro-N-(2-[4-(2-n-propoxyethyl)-2-methylphenoxy]ethyl)-N-(imidazol-1-ylcarbonyl)-6-methyl-4-pyrimidine amine, 5-bromo-N-(2-[4-(2-ethoxyethyl)-2-methylphenoxy]ethyl)-N-(imidazol-1-ylcarbonyl)-6-methyl-4-pyrimidine amine, N-(2-[4-(2-ethoxyethyl)-2methylphenoxy]ethyl)-N-(imidazol-1-ylcarbonyl)-4-cyclopentapyrimidine amine, 5-chloro-N-(2-[4-(2-allyloxyethyl)-2-methylphenoxy]ethyl)-N-(imidazol-1-ylcarbonyl)-6-methyl-4-pyrimidine amine, N-(2-[4-(4-methoxybutyl)-2-methylphenoxy]ethyl)-N-(imidazol-1-ylcarbonyl)-4-quinazoline amine, 5-chloro-N-n-decyl-N-(imidazol-1-ylcarbonyl)-6-ethyl-4-pyrimidine amine and acid addition salts thereof.

* * * * *